United States Patent
Chung et al.

(10) Patent No.: US 12,357,443 B2
(45) Date of Patent: Jul. 15, 2025

(54) BENIGN PROSTATIC HYPERPLASIA TREATMENT DEVICE

(71) Applicant: CEDARS HEALTH, INC., Hanam-si (KR)

(72) Inventors: Yoon Ho Chung, Seoul (KR); Geon Sun Park, Seoul (KR)

(73) Assignee: CEDARS HEALTH INC., Hanam-si (KR)

( * ) Notice: Subject to any disclaimer, the term of this patent is extended or adjusted under 35 U.S.C. 154(b) by 717 days.

(21) Appl. No.: 17/730,214

(22) Filed: Apr. 27, 2022

(65) Prior Publication Data

US 2022/0249219 A1      Aug. 11, 2022

Related U.S. Application Data

(63) Continuation-in-part of application No. 17/362,993, filed on Jun. 30, 2021, now Pat. No. 11,337,689.

(30) Foreign Application Priority Data

Aug. 31, 2020   (KR) ........................ 10-2020-0109927

(51) Int. Cl.
    *A61F 2/00*      (2006.01)
    *A61B 17/34*     (2006.01)

(52) U.S. Cl.
    CPC ........ *A61F 2/0045* (2013.01); *A61B 17/3468* (2013.01); *A61F 2220/0075* (2013.01)

(58) Field of Classification Search
    CPC ............ A61B 17/0469; A61B 17/0401; A61B 17/0467; A61B 17/0482; A61B 2017/00274; A61B 2017/00296; A61B 2017/0409; A61B 2017/0464
    See application file for complete search history.

(56) References Cited

U.S. PATENT DOCUMENTS

| | | | | |
|---|---|---|---|---|
| 5,810,848 | A * | 9/1998 | Hayhurst | A61B 17/04 606/232 |
| 6,972,027 | B2 * | 12/2005 | Fallin | A61B 17/0401 606/232 |
| 7,601,165 | B2 * | 10/2009 | Stone | A61B 17/0482 606/232 |
| 8,236,011 | B2 * | 8/2012 | Harris | A61B 90/94 606/232 |
| 8,790,369 | B2 * | 7/2014 | Orphanos | A61B 17/0469 606/232 |
| 9,402,711 | B2 * | 8/2016 | Catanese, III | A61F 2/04 |
| 9,750,492 | B2 * | 9/2017 | Ziniti | A61B 17/0487 |
| 10,105,132 | B2 * | 10/2018 | Lamson | A61B 18/1492 |

(Continued)

*Primary Examiner* — Phong Son H Dang
(74) *Attorney, Agent, or Firm* — Quantum Patent Law Firm; Seongyoune Kang

(57) ABSTRACT

Disclosed herein is a benign prostatic hyperplasia treatment device. The benign prostatic hyperplasia treatment device includes: anchor assemblies including a first anchor arranged at the outer surface of the prostate gland, which obstructs the prostatic urethra, a second anchor arranged inside the prostate gland to be opposed to the first anchor, and a ligature connecting the first anchor and the second anchor with each other so that the second anchor compresses the prostate tissue to secure the opening of the prostatic urethra; and a sheath inserted into the urethra and having a needle, which guides the anchor assembly to be deployed at the prostate gland.

3 Claims, 26 Drawing Sheets

(56) References Cited

U.S. PATENT DOCUMENTS

| | | | | |
|---|---|---|---|---|
| 10,130,353 | B2* | 11/2018 | Catanese, III | A61B 17/0644 |
| 10,143,461 | B2* | 12/2018 | Catanese | A61B 17/42 |
| 10,265,061 | B2* | 4/2019 | Johnston | A61B 17/0401 |
| 10,299,780 | B2* | 5/2019 | Catanese, III | A61B 17/0487 |
| 10,349,932 | B2* | 7/2019 | Catanese, III | A61B 17/0401 |
| 10,441,273 | B2* | 10/2019 | Hirotsuka | A61B 17/0401 |
| 2002/0019649 | A1* | 2/2002 | Sikora | A61B 17/0401 |
| | | | | 606/232 |
| 2006/0190042 | A1* | 8/2006 | Stone | A61B 17/0401 |
| | | | | 606/232 |
| 2006/0217762 | A1* | 9/2006 | Maahs | A61B 17/0482 |
| | | | | 606/213 |
| 2008/0140093 | A1* | 6/2008 | Stone | A61B 17/0469 |
| | | | | 606/228 |
| 2008/0195145 | A1* | 8/2008 | Bonutti | A61B 17/0469 |
| | | | | 606/205 |
| 2009/0112234 | A1* | 4/2009 | Crainich | A61B 17/0469 |
| | | | | 606/144 |
| 2010/0023022 | A1* | 1/2010 | Zeiner | A61B 17/0401 |
| | | | | 606/139 |
| 2010/0023024 | A1* | 1/2010 | Zeiner | A61B 17/0469 |
| | | | | 606/144 |
| 2010/0030262 | A1* | 2/2010 | McLean | A61B 17/0401 |
| | | | | 606/232 |
| 2011/0060349 | A1* | 3/2011 | Cheng | A61B 17/0469 |
| | | | | 606/139 |
| 2011/0082471 | A1* | 4/2011 | Holcomb | A61B 17/0401 |
| | | | | 606/139 |
| 2011/0160747 | A1* | 6/2011 | McLean | A61F 2/04 |
| | | | | 606/139 |
| 2018/0256142 | A1* | 9/2018 | Tong | A61B 17/0401 |

* cited by examiner (a)

(b)

(a)

(b)

BENIGN PROSTATIC HYPERPLASIA TREATMENT DEVICE

TECHNICAL FIELD

The present invention relates to a benign prostatic hyperplasia treatment device, and more particularly, to a benign prostatic hyperplasia treatment device, which can continuously open the prostatic urethra by ligating an enlarged prostate after pushing the enlarged prostate out of the urethra.

BACKGROUND ART

In general, benign prostatic hyperplasia is a symptom that causes the prostate to become enlarged abnormally and causes urethrophraxis since the abnormally enlarged prostate blocks the prostatic urethra below the bladder, so that urine is not excreted smoothly.

A person who has the benign prostatic hyperplasia experiences great inconveniences in his daily life due to various symptoms, such as frequent urination, urination at night, weak urinary stream, feeling of residual urine, and others.

In order to treat such benign prostatic hyperplasia, a benign prostatic hyperplasia treatment method illustrated in FIG. 1 has been carried out.

When the benign prostatic hyperplasia occurs, as shown in FIG. 1(a), a pair of prostate lobes A and B enlarges at both sides of the urethra C and blocks the urethra C. As shown in FIG. 1(b), an operator inserts a cystoscope 10 into the urethra, inserts a medical ligator 11 disposed at an end portion of the cystoscope 10 through the prostate lobes A and B as shown in FIG. 1(c), puts a first implant 20 at an upper portion of the left prostate lobe A as shown in FIG. 1(d), and puts a second implant 20a at an upper portion of the right prostate lobe B as shown in FIG. 1(e).

After that, as shown in FIG. 1(f), the operator puts a third implant 20b and a fourth implant 20c respectively at a lower portion of the left prostate lobe A and a lower portion of the right prostate lobe B.

In this instance, the implants 20, 20a, 20b and 20c have external implants 21 arranged on the outside of the prostate lobes A and B and internal implants 23 arranged near the urethra. Each of the external implants 21 and each of the internal implants 23 are connected to each other by a ligature 25, and the internal implants 23 compress the prostate lobes A and B outwards based on the length of the ligature 25 in order to open the urethra.

However, such a benign prostatic hyperplasia treatment method has a disadvantage in that the area of the prostate tissue compressed by one implant 20 is limited to the size of the internal implant 23.

Moreover, the prostate tissue (a) between the internal implant at the upper portion and the internal implant at the lower portion is not compressed but still remains in the enlarged state toward the urethra since there is an interval between the implant 20 arranged at the upper portion and the implant 20b arranged at the lower portion, so that the prostate tissue is not compressed continuously but just a part abutting the internal implant 23 is compressed partially.

PATENT LITERATURE

Patent Documents

Patent Document 1: Korean Patent No. 10-1534820 entitled "Implant for treating benign prostatic hyperplasia"

Patent Document 2: U.S. patent Ser. No. 10/349,932 entitled "Anchor delivery system"

DISCLOSURE

Technical Problem

Accordingly, the present invention has been made in an effort to solve the above-mentioned problems occurring in the prior arts, and it is an object of the present invention to provide a benign prostatic hyperplasia treatment device that can adjust an area of compression by a pair of anchors arranged at upper and lower portions of the prostate lobe and connected with each other by a ligature.

It is another object of the present invention to provide a benign prostatic hyperplasia treatment device that can adjust the length of the ligature that connects a pair of the anchors in order to continuously compress the prostate gland according to patients' prostate sizes.

Technical Solution

To achieve the above objects, the present invention provides a benign prostatic hyperplasia treatment device including: anchor assemblies including a first anchor arranged at the outer surface of the prostate gland, which obstructs the prostatic urethra, a second anchor arranged inside the prostate gland to be opposed to the first anchor, and a ligature connecting the first anchor and the second anchor with each other so that the second anchor compresses the prostate tissue to secure the opening of the prostatic urethra; and a sheath inserted into the urethra and having a needle, which guides the anchor assembly to be deployed at the prostate gland.

Moreover, the benign prostatic hyperplasia treatment device further includes: a needle manipulation part for manipulating movement of the needle so that the needle is deployed through an end portion of the sheath; a thread winder disposed at one side of the needle manipulation part and winding the ligature thereon to adjust intensity with which the anchor assemblies compress the prostate gland; and a handle frame part which supports the end portion of the sheath, the needle manipulation part and the thread winder and is grasped by an operator, wherein the ligature includes: a length-adjustable loop joined to the first anchor and the second anchor to be adjustable in length; a free end extending from the length-adjustable loop; and a slip knot for connecting the length-adjustable loop to the free end so as to adjust the length of the length-adjustable loop.

Furthermore, the thread winder winds the free end to adjust the length of the length-adjustable loop so that the second anchor compresses the prostate tissue.

Advantageous Effects

Compared with the conventional benign prostatic hyperplasia treatment device which partially compresses the prostate tissues, the benign prostatic hyperplasia treatment device according to the present invention has an advantage in that urine flow rate increases since the prostate tissue compressed by the ligature and a pair of the anchors is continuous, and is more effective for patients who have a large prostate gland.

Furthermore, the benign prostatic hyperplasia treatment device according to the present invention has another advantage in that the operator can adjust intensity with which to compress the prostate gland as much as the operator wants since the operator adjusts the length of the ligature by winding a free end of the ligature.

Therefore, the benign prostatic hyperplasia treatment device according to the present invention can adjust the compression level according to various symptoms of benign prostatic hyperplasia presented by patients.

A treatment method using the benign prostatic hyperplasia treatment device according to the present invention does not need general anesthesia or long operation time like laser surgery or electrical surgery using thermal energy.

Additionally, the benign prostatic hyperplasia treatment device according to the present invention makes quick operation time and local anesthesia possible through a simple anchor installation method, and is not accompanied by side effects, such as retrograde ejaculation, impotence or hematuria, since the prostate tissues are not resected. In addition, because the benign prostatic hyperplasia treatment device according to the present invention is minimally invasive, if it is ineffective, a patient can have another operation any time.

MODE FOR INVENTION

Hereinafter, preferred embodiments of the present invention will now be described in detail with reference to the attached drawings, in which like reference numbers denote corresponding parts throughout the drawings.

The terms "comprising" and "including" in the discussion directed to the present invention and the claims are used in an open-ended fashion and thus should be interrupted to mean "including", but not limited thereto.

Figure 2:
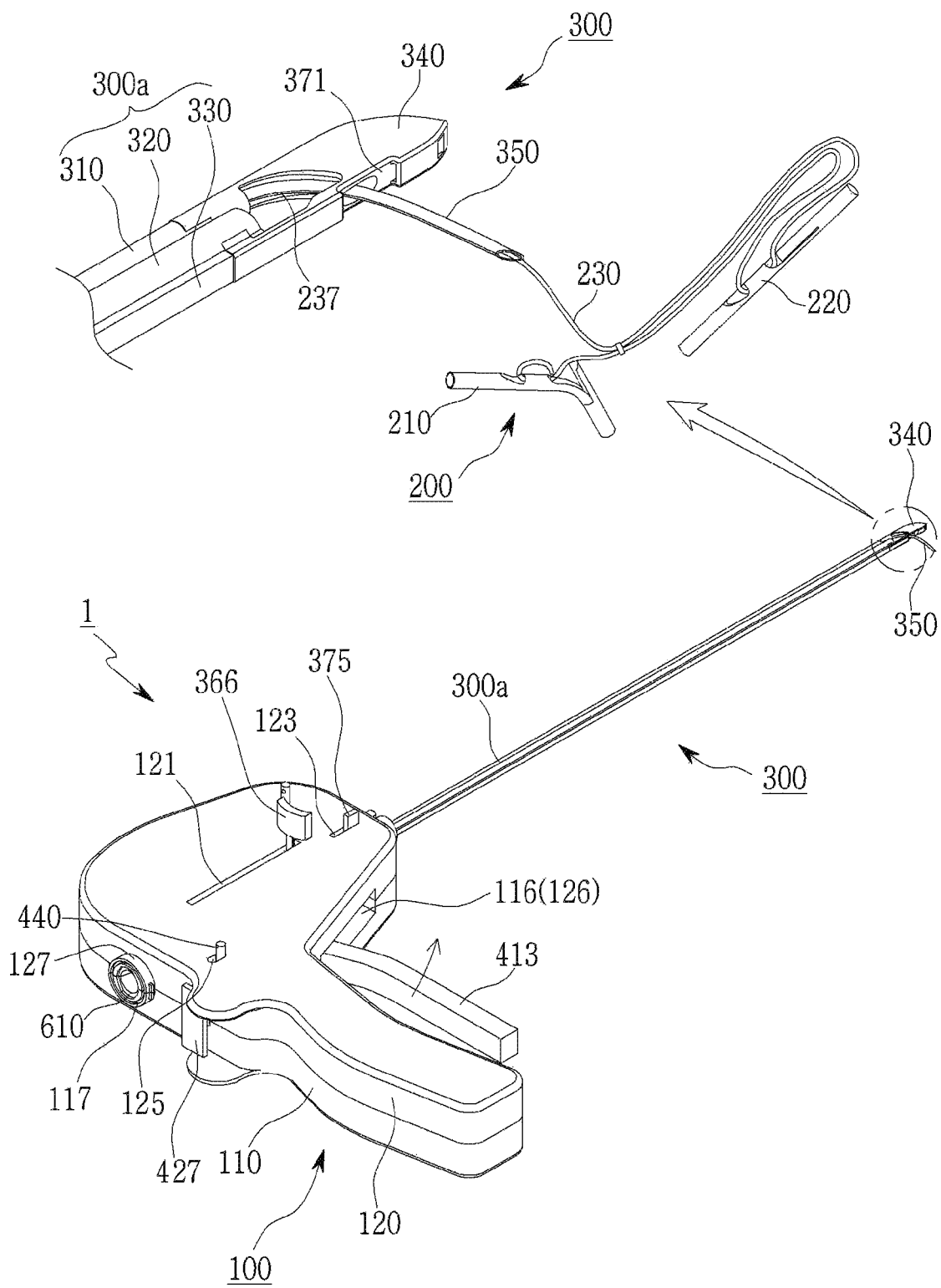
FIG. 2 is a perspective view showing a structure of a benign prostatic hyperplasia treatment device according to an embodiment of the present invention.
Figure 3:
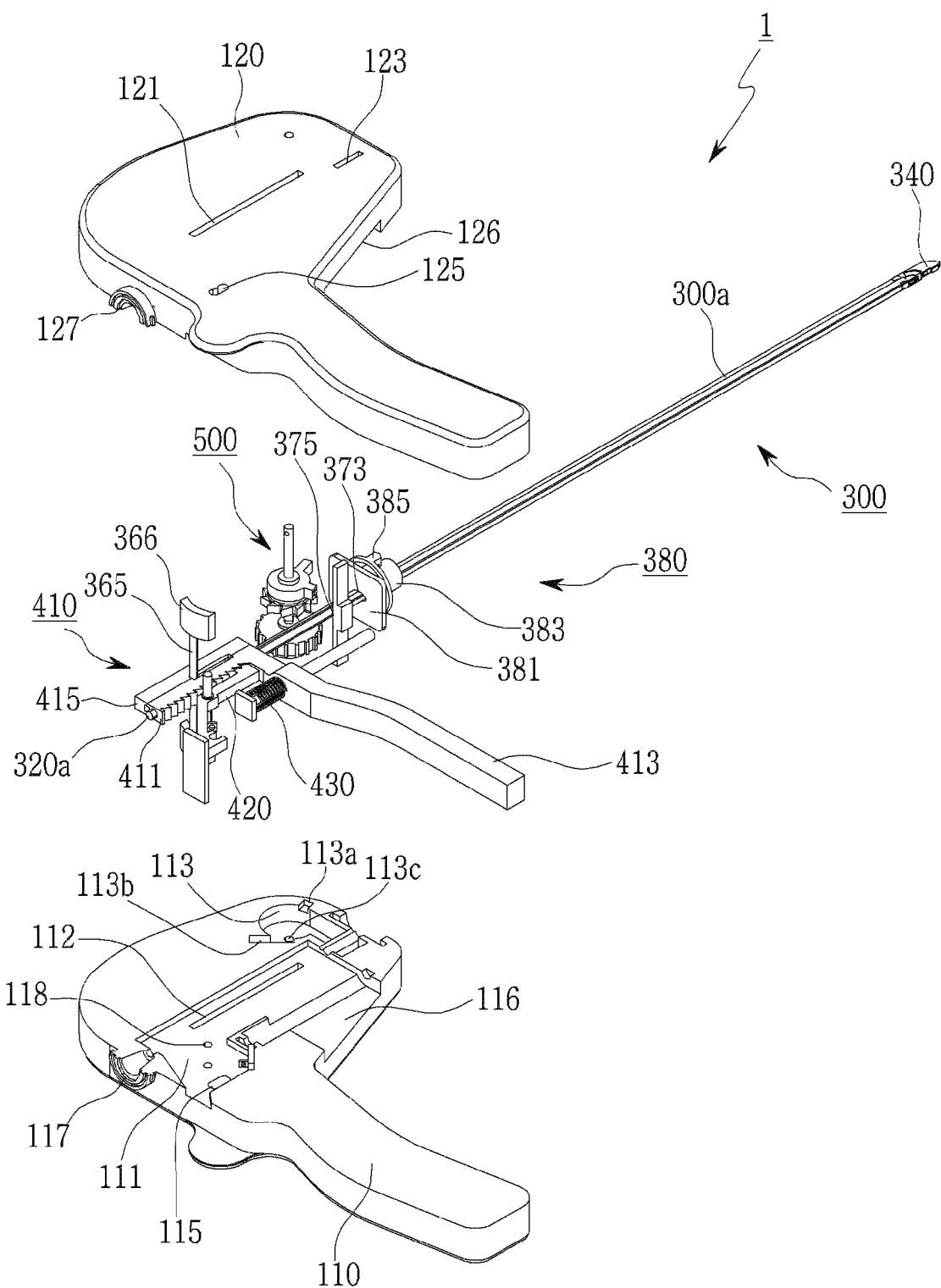
FIGS. 3 to 5 are exploded perspective views showing the structure of the benign prostatic hyperplasia treatment device according to the embodiment of the present invention.
Figure 4:
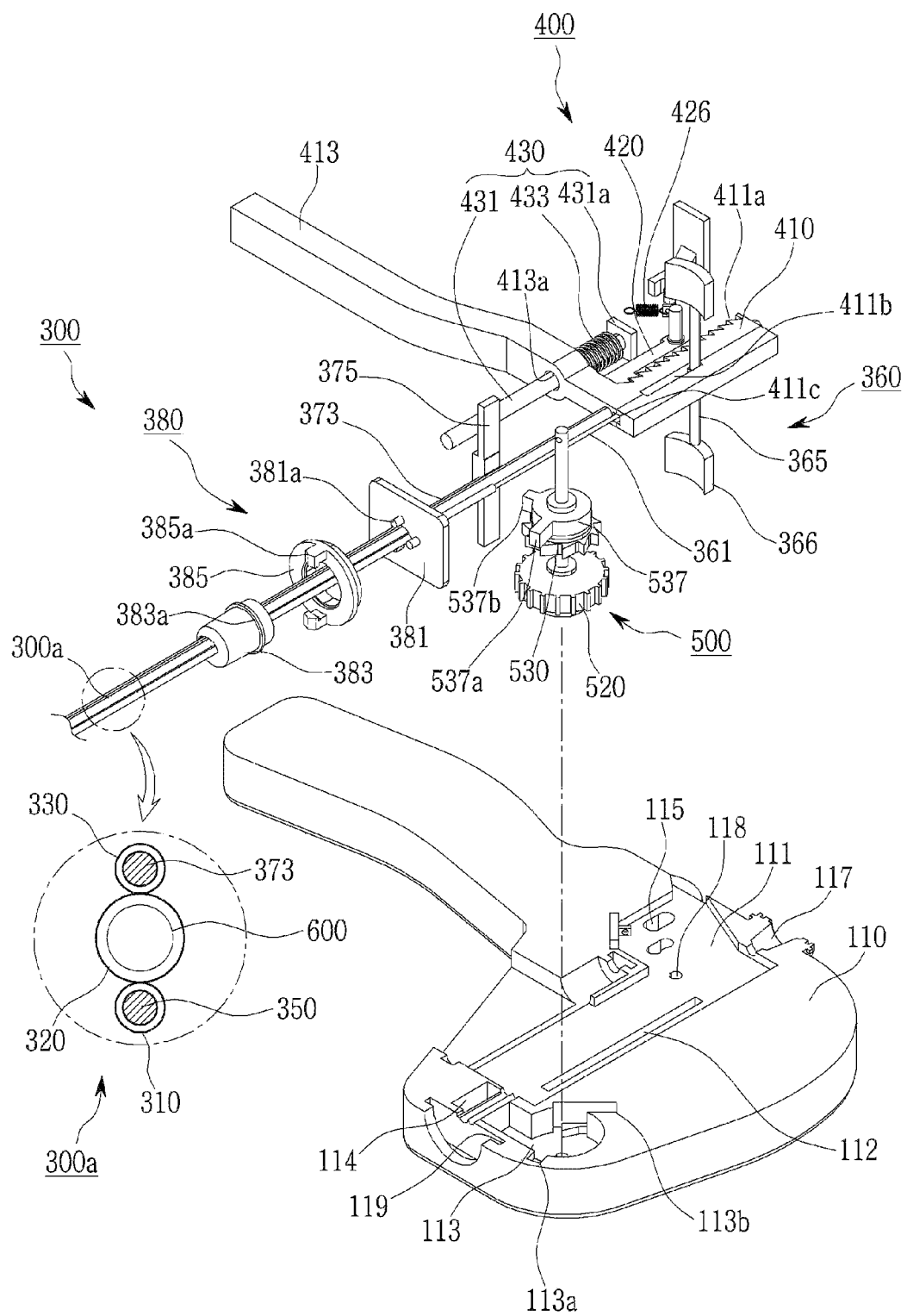
Figure 5:
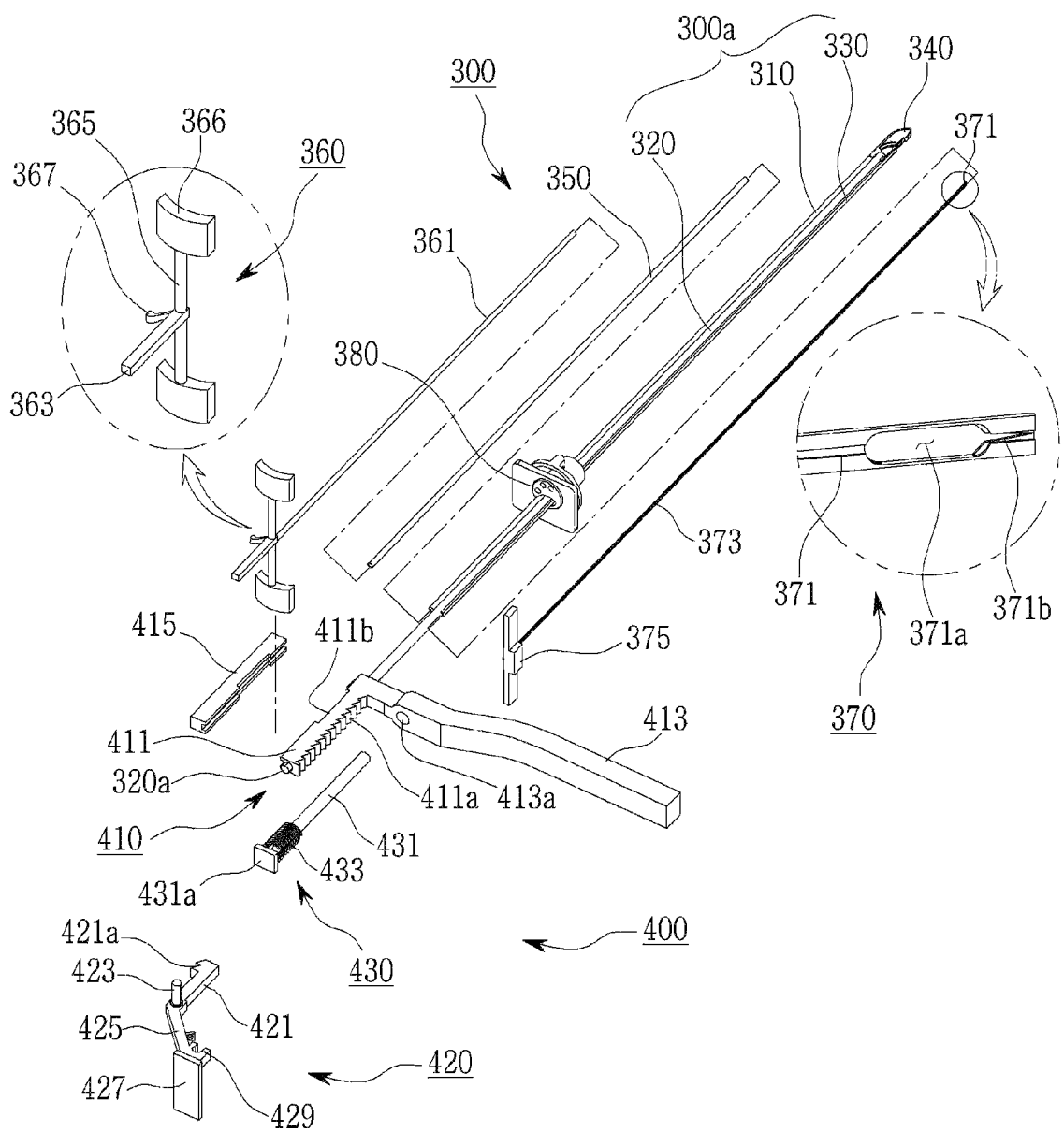
Figure 6:
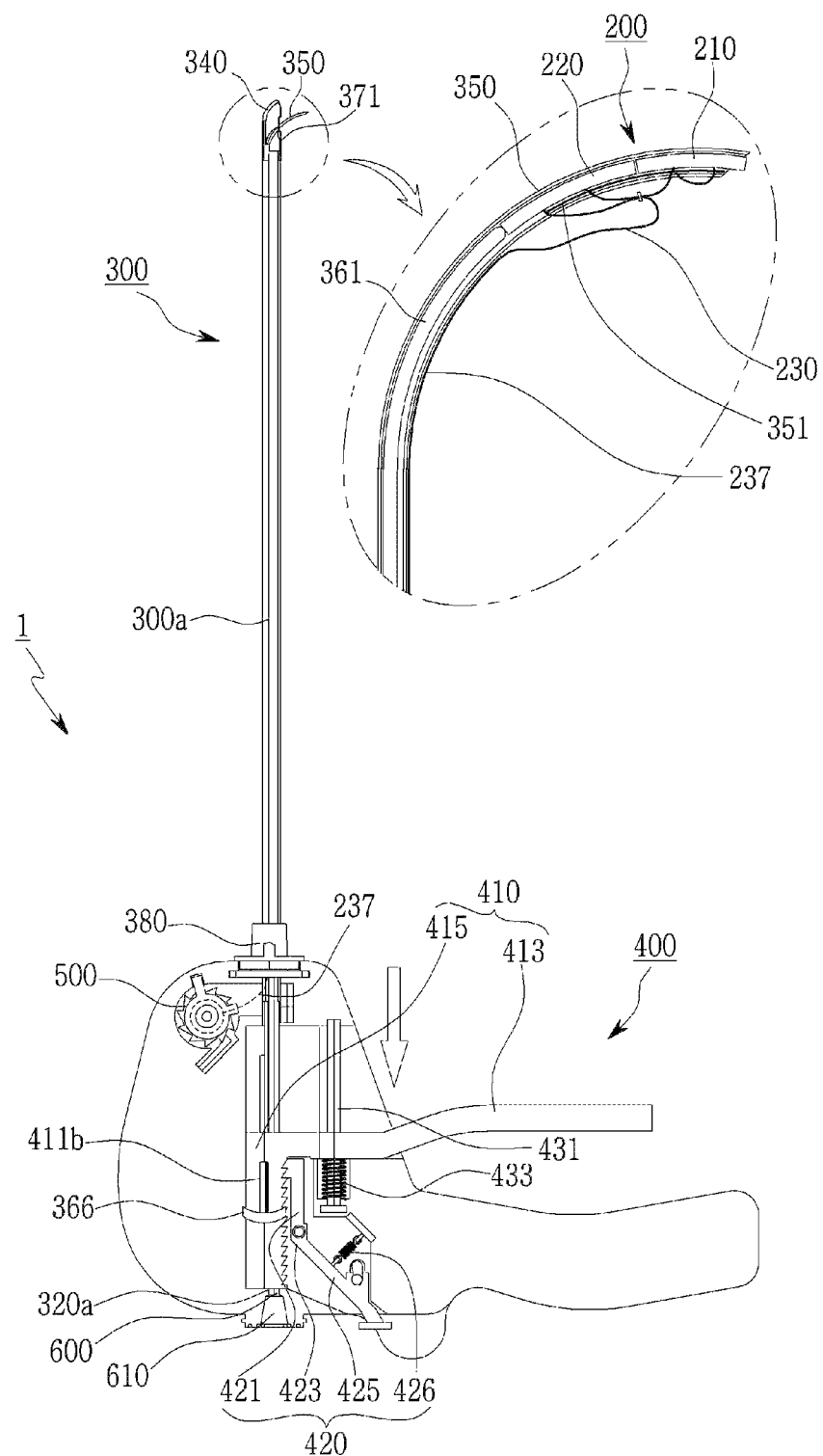
FIG. 6 is a side view showing a lateral structure of the benign prostatic hyperplasia treatment device according to the embodiment of the present invention.

FIG. 2 is a perspective view showing a structure of a benign prostatic hyperplasia treatment device 1 according to an embodiment of the present invention, FIGS. 3 to 5 are exploded perspective views showing the structure of the benign prostatic hyperplasia treatment device 1 according to the embodiment of the present invention, and FIG. 6 is a side view showing a lateral structure of the benign prostatic hyperplasia treatment device 1 according to the embodiment of the present invention.

The benign prostatic hyperplasia treatment device 1 according to the embodiment of the present invention includes: a handle frame part 100 that fixes each of the components and an operator grips with the hand; an anchor assembly 200 which is deployed at the prostate lobes A and B to open the urethra by compressing the prostate tissues blocking the urethra; a sheath 300 which extends from the front end of the handle frame part 100 to a predetermined length and is inserted into the urethra (C) to guide a needle 350 accommodated therein so that an anchor assembly 200 is deployed at the prostate lobes A and B; a needle manipulating part 400 which is disposed in the handle frame part 100 to adjust the position of the needle 350 and is manipulated by the operator so that the anchor assembly 200 comes out of the needle 350; and a thread winder 500 which is rotatably disposed in the handle frame part 100 to wind a ligature 230 of the anchor assembly 200 and adjusts the length of the ligature 230 so that the anchor assembly 200 compresses the prostate lobes A and B.

The benign prostatic hyperplasia treatment device 1 according to the embodiment of the present invention can continuously compress the prostate gland, which obstructs the urethra, with compression level desired by the operator using a pair of the anchor assemblies 200. Therefore, the benign prostatic hyperplasia treatment device 1 according to the embodiment of the present invention can adjust the length and the depth of compression to the prostate gland according to symptoms of benign prostatic hyperplasia presented by patients, and can increase urine flow rate.

As shown in FIGS. 2 to 4, the handle frame part 100 is combined with the rear of the sheath 300 and contains the needle manipulating part 400 therein. The operator can manipulate the sheath 300 and the needle manipulating part 400 with the handle frame part 100 in his or her hand in order to insert the sheath 300 into the urethra, and then, adjust the positions of the needle 350 and the anchor assembly 200 in order to deploy the anchor assembly 200 at the prostate gland.

The handle frame part 100 is formed by a releasable combination of a left frame 110 and a right frame 120 which are respectively arranged at the left and the right. The left frame 110 and the right frame 120 are generally formed in a handle shape to be grasped in the hand.

Needle manipulating part receiving grooves 111 are formed on internal plate surfaces of the left frame 110 and the right frame 120 to a predetermined depth so that the position of the needle manipulating part 400 can be fixed between the left frame 110 and the right frame 120. Moreover, a needle holder 410 of the needle manipulating part 400 can move forwards and backwards stably inside the needle manipulating part receiving groove 111.

A thread winder receiving recess 113 is formed at an upper portion of the needle manipulating part receiving groove 111 to be hollow to a predetermined depth relative to the plate surface. As shown in FIG. 4, a winder gear 530 of the thread winder 500 is accommodated in the thread winder receiving recess 113. A shaft hole 113c into which a winder shaft 510 is inserted is bored into the bottom surface of the thread winder receiving recess 113, and a winder fixing groove 113a and a limit bar receiving groove 113b are formed on the outer circumferential surface of the thread winder receiving recess 113 outwardly in a radial direction.

A position fixing protrusion 537a of a thread guide cap 537 of the winder gear 530 is accommodated in the winder fixing groove 113a. Therefore, the winder gear 530 is rotated inside the thread winder receiving groove 113, and the thread guide cap 537 is not rotated but is fixed in its position.

A one-way rotation limit bar 540 of the thread winder 500 is accommodated in the limit bar receiving groove 113b to limit the rotational direction so that the winder gear 530 rotates in just one direction.

The shaft hole 113c is bored into the bottom surface of the winder fixing groove 113a. The winder shaft 510 of the thread winder 500 is inserted into the shaft hole 113c.

The left frame 110 and the right frame 120 respectively include pusher movement slits 112 and 121 formed in the opposite direction to each other, blade button movement slits 114 and 123 formed in the opposite direction to each other, and locking member movement grooves 115 and 125 formed in the opposite direction to each other. As shown in FIG. 2, a pusher button 366 is extended outwards from the pusher movement slits 112 and 121 to a predetermined length, a blade pressing button 375 is extended outwards from the blade button movement slits 114 and 123 to a predetermined length, and a trigger locking member 440 is extended outwards from the locking member movement grooves 115 and 125 to a predetermined length.

The operator presses the pusher button 366 and the trigger locking member 440, which are extended from both sides of the left frame 110 and the right frame 120 to the predetermined length, with his or her hand in order to simply adjust the position of the needle 350 and the position of the anchor assembly 200 by adjusting positions of the pusher button 366 and the trigger locking member 440 back and forth, and manipulates the blade pressing button 375 to cut a free end 237.

In the meantime, lever movement paths 116 and 126 are respectively formed at the front of the left frame 110 and at the front of the right frame 120 in order to guide back-and-forth movement of a pulling lever 413 of a needle holder 410 of the needle manipulating part 400.

Furthermore, endoscope insertion holes 117 and 127 into which a transurethral endoscope is inserted are respectively formed at the rear of the left frame 110 and at the rear of the right frame 120 so that the operator can inspect the inside of the prostate gland during a surgical operation.

Figure 7:
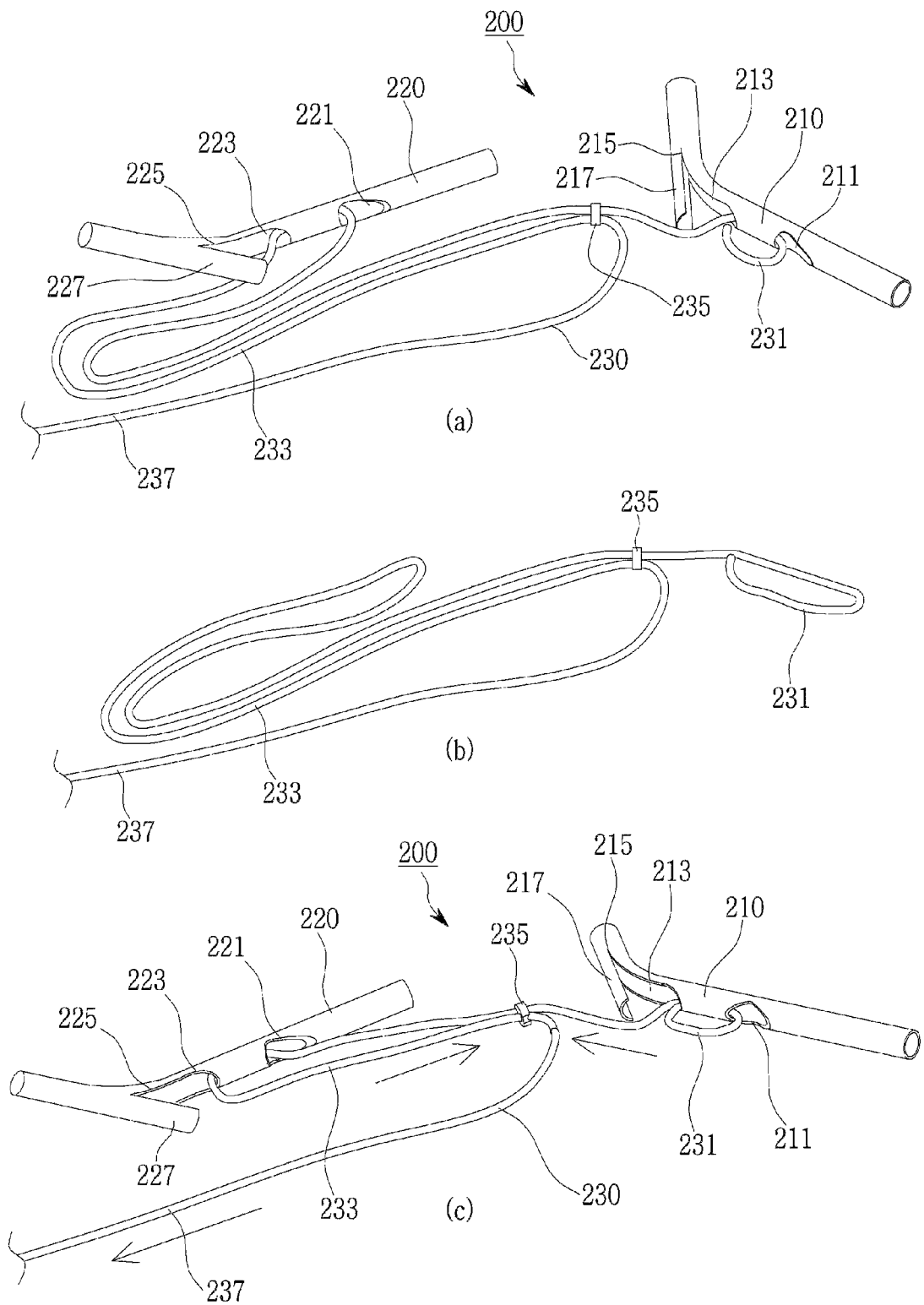
FIG. 7 is a perspective view showing a structure of an anchor assembly of the benign prostatic hyperplasia treatment device according to the embodiment of the present invention.
Figure 8:
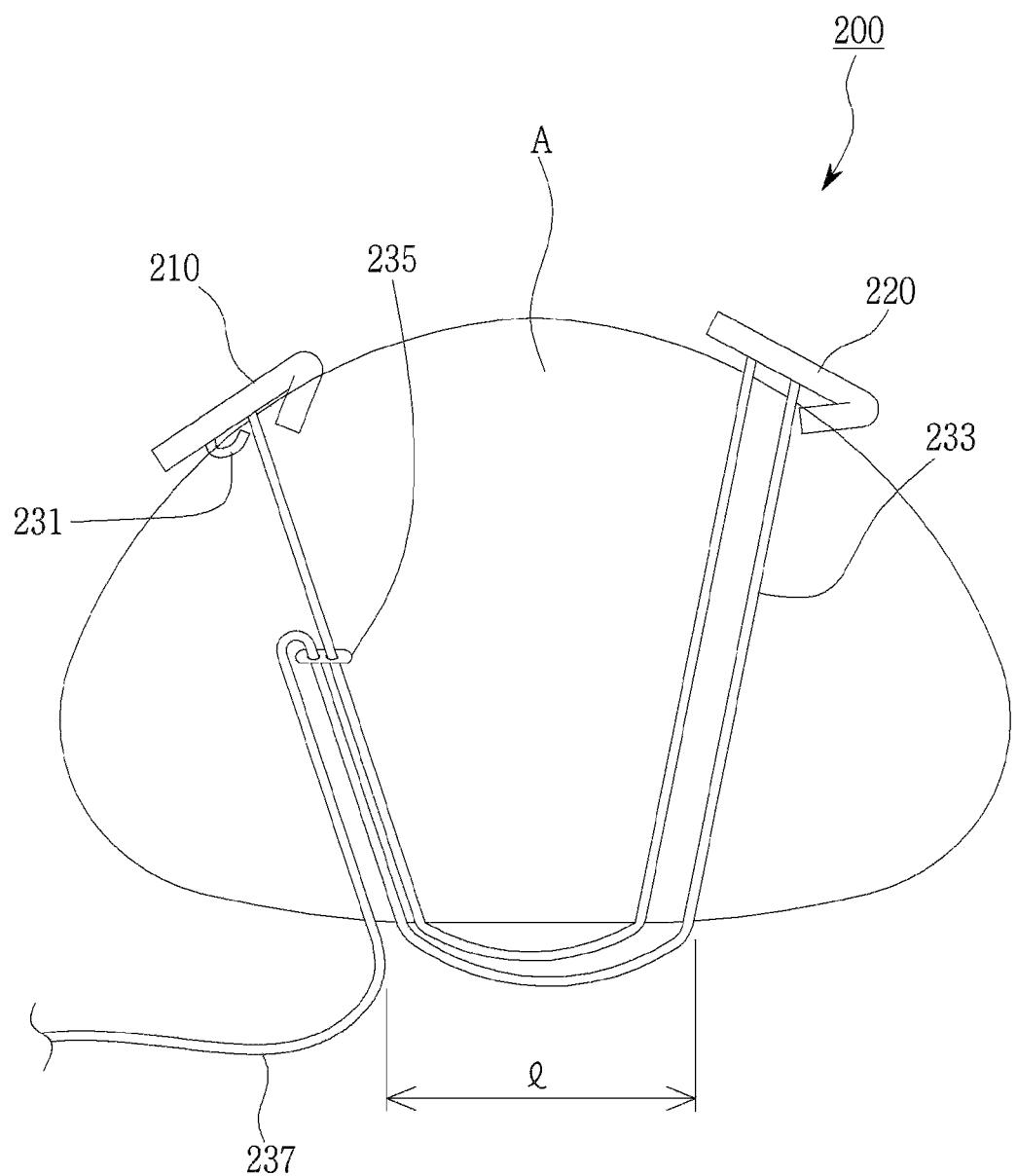
FIG. 8 is an exemplary view showing a state where the anchor assembly of the benign prostatic hyperplasia treatment device according to the embodiment of the present invention is deployed at a left prostate lobe.

The anchor assembly 200 is deployed at the prostate gland of the patient and compresses the prostate gland so that the urethra is opened. When a pair of the anchor assemblies 200 is deployed at the left prostate lobe A and the right prostate lobe B, the medical operation using the benign prostatic hyperplasia treatment device 1 according to the embodiment of the present invention is finished. FIG. 7 is a perspective view showing structure of one anchor assembly 200, and FIG. 8 is an exemplary view showing a state after the anchor assembly 200 is deployed at a left prostate lobe A and before the length is adjusted.

As shown in FIG. 7(a), the anchor assembly 200 includes the first anchor 210, the second anchor 220, and the ligature 230 for connecting the first anchor 210 and the second anchor 220 with each other. The first anchor 210 is formed in a hollow tube shape. A first thread hole 211 and a second thread hole 213 into which the ligature 230 is inserted are formed in the surface of the first anchor 210. The second thread hole 213 has bent slits 215 of a predetermined length formed at both sides thereof. By the bent slits 215, a bent plate 217 is bent to be inclined at a predetermined angle and the second thread hole 213 is expanded in size.

The ligature 230 is inserted into the first thread hole 211, and then, is passed through the second thread hole 213. In this instance, because the internal space of the first anchor 210 is narrow, it is not easy to pass the ligature 230 inserted into the first thread hole 211 through the second thread hole 213. Therefore, the bent plate 217 is bent by the bent slits 215 and the second thread hole 213 is expanded, so that the ligature 230 can be passed through easily.

Figure 16:
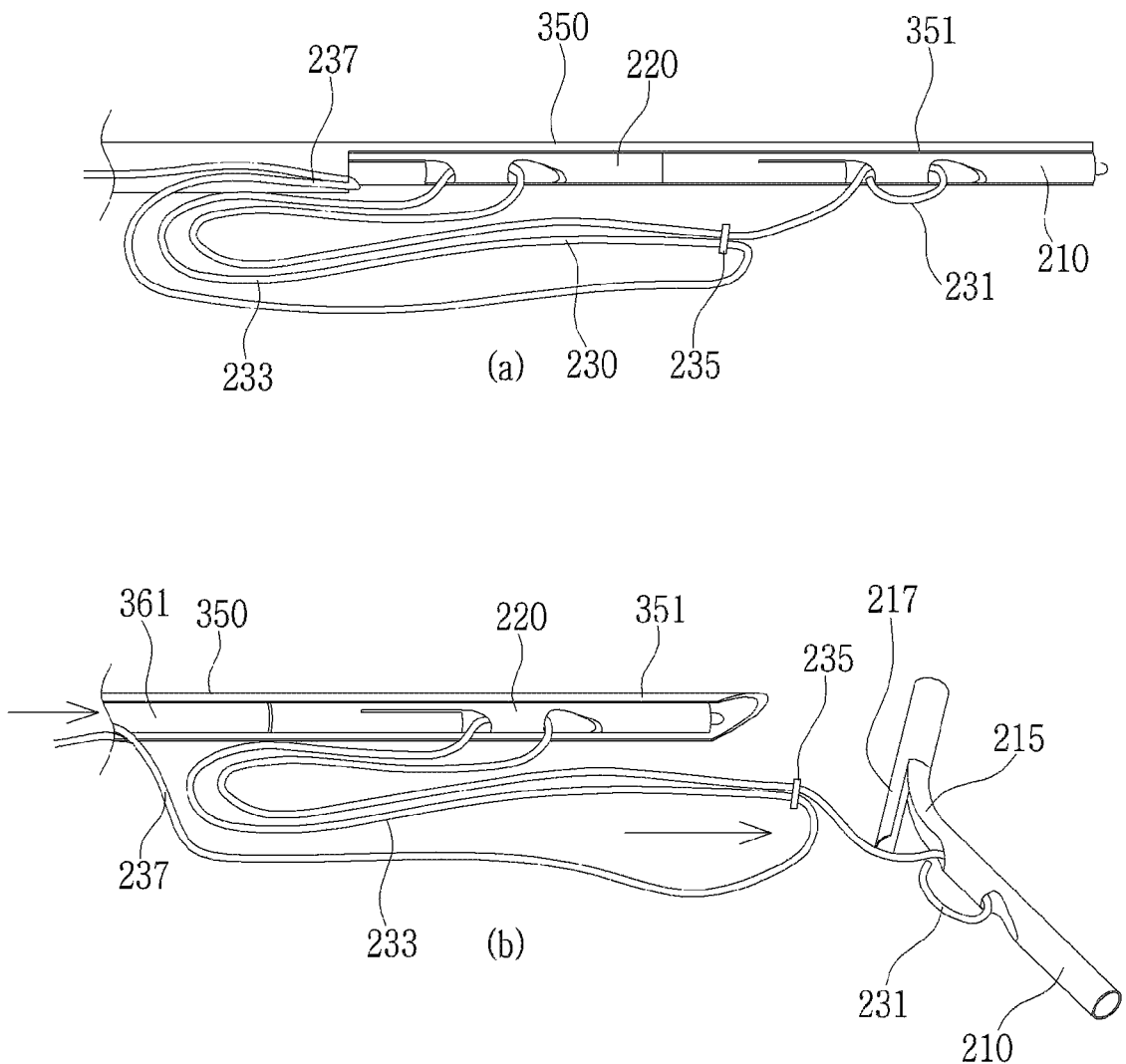

The first anchor 210 and the second anchor 220 are made of metal or metal alloy, are preferably made of nitinol and have the same structure. The first anchor 210 and the second anchor 220 are bent by the bent slits 215, but as shown in FIG. 16(a), are elastically transformed according to the shape of the needle 350 when being accommodated in the needle 350. As shown in FIG. 16(b), the bent plates 217 and 227 are returned to their original state when the first anchor 210 and the second anchor 220 are outside the needle 350.

The bent plate 217 is bent relative to the outer surface of the first anchor 210 due to the bent slit 215, and prevents the first anchor 210 located on the outer surface of the prostate gland from moving reversely through the hole in the prostate gland formed by the needle 350.

That is, during the surgical operation, when the needle 350 pierces the prostate lobe A and puts the first anchor 210 outside the prostate lobe A, the first anchor 210 is bent as the bent plate 217 is bent elastically. The bent first anchor 210 is caught by the hole in the prostate gland formed by the needle 350 and is prevented from the reverse movement, and then, is put on the surface of the prostate lobe A stably.

The ligature 230 connects the first anchor 210 and the second anchor 220 with each other in such a way as to be adjustable in length. The first anchor 210 and the second anchor 220 do not independently compress specific parts of the prostate gland but an arc-shaped or a 'U'-shaped line formed by the first anchor 210, the second anchor 220 and the ligature 230 continuously compresses the prostate gland.

As shown in FIG. 7(b), the ligature 230 includes a fixed end 231 joined to the first anchor 210, a length-adjustable loop 233 joined to the second anchor 220, the free end 237 connected to an end portion of the length-adjustable loop 233, and a slip knot 235 for tying the free end 237 and the length-adjustable loop 233.

The fixed end 231 is tied to the first thread hole 211 and the second thread hole 213 of the first anchor 210 to be fixed in position. The length-adjustable loop 233 is inserted into the first thread hole 221 of the second anchor 220, and then exits through the second thread hole 223 of the second anchor 220 to be formed in a loop shape. The length-adjustable loop 233 is formed between the fixed end 231 and the free end 237 by the slip knot 235.

As shown in FIG. 7(C), because the first anchor 210 joined to the fixed end 231 is fixed in position when the free end 237 is pulled, the length-adjustable loop 233 gets shorter so as to compress the prostate gland surrounded by it.

As shown in FIG. 8, when the first anchor 210 and the second anchor 220 are arranged outside the prostate lobes A and B, the ligature 230 is arranged loosely. In the above state, when the operator rotates a winder handle 520 to wind the free end 237 on the winder gear 530, the free end 237 gets shorter and the length-adjustable loop 233 also gets shorter so as to compress the prostate lobes A and B.

That is, as shown in FIG. 19(b), when the first anchor 210 and the second anchor 220 are arranged outside the prostate gland, the ligature 230 is connected loosely. When the operator pulls the free end 237 using the winder handle 520 to tighten the ligature 230, as shown in FIG. 19(c), the first anchor 210, the second anchor 220 and the ligature 230 continuously surround and compress the prostate lobes A and B. Because the first anchor 210 and the second anchor 220 are connected with each other by the ligature 230, the space between the first anchor 210 and the second anchor 220 is also compressed continuously so that the urethra (C) is opened.

The sheath 300 guides the anchor assembly 200 toward the prostate lobes A and B with the needle 350. As shown in FIGS. 5 and 6, the rear end of the sheath 300 is combined with the handle frame part 100, and the front end extends from the handle frame part 100 to a predetermined length and is inserted into the urethra (C) through an outer sheath (S).

Figure 18:
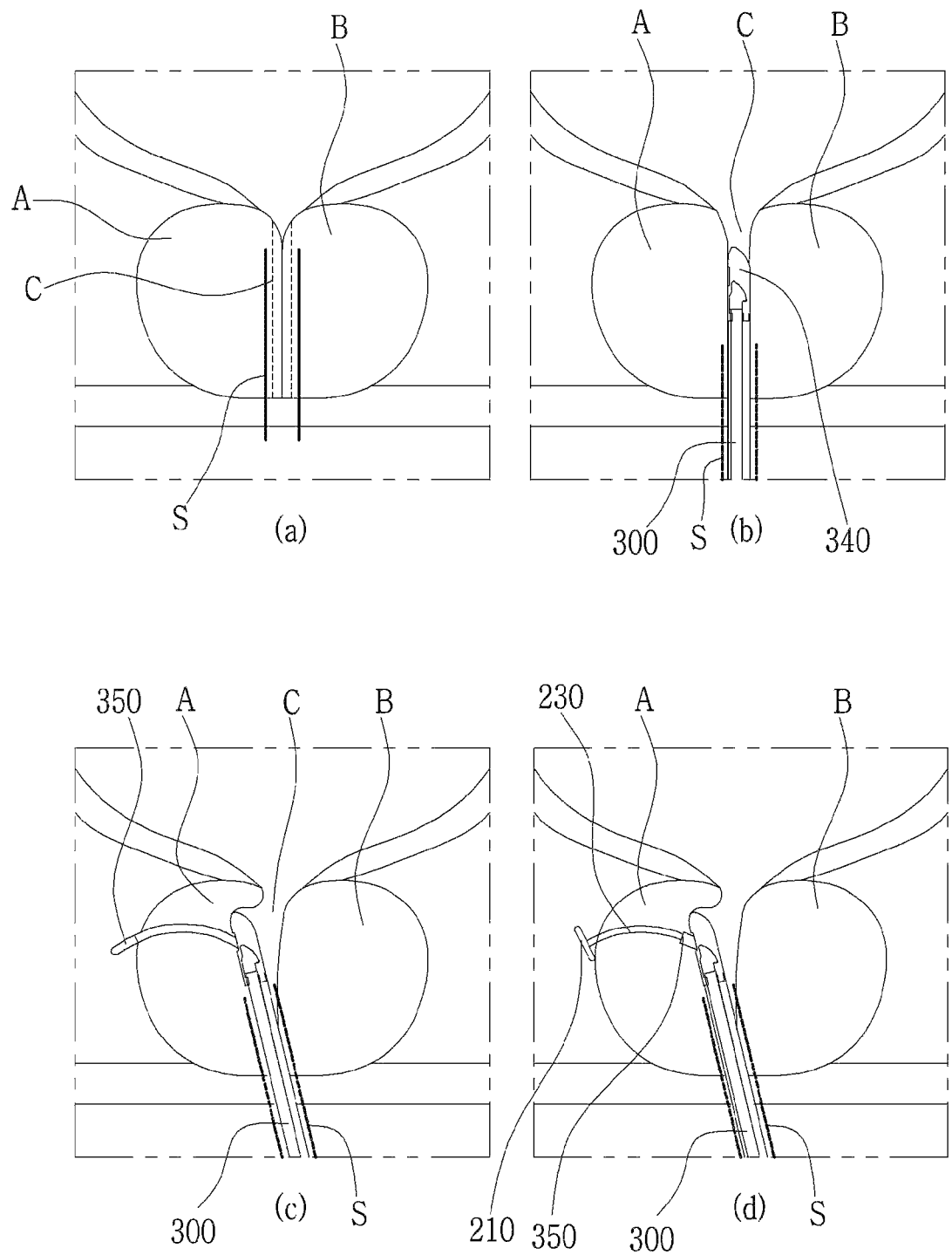
FIGS. 18 and 19 are exemplary views schematically showing a treatment process of benign prostatic hyperplasia using the benign prostatic hyperplasia treatment device according to the embodiment of the present invention.
Figure 19:
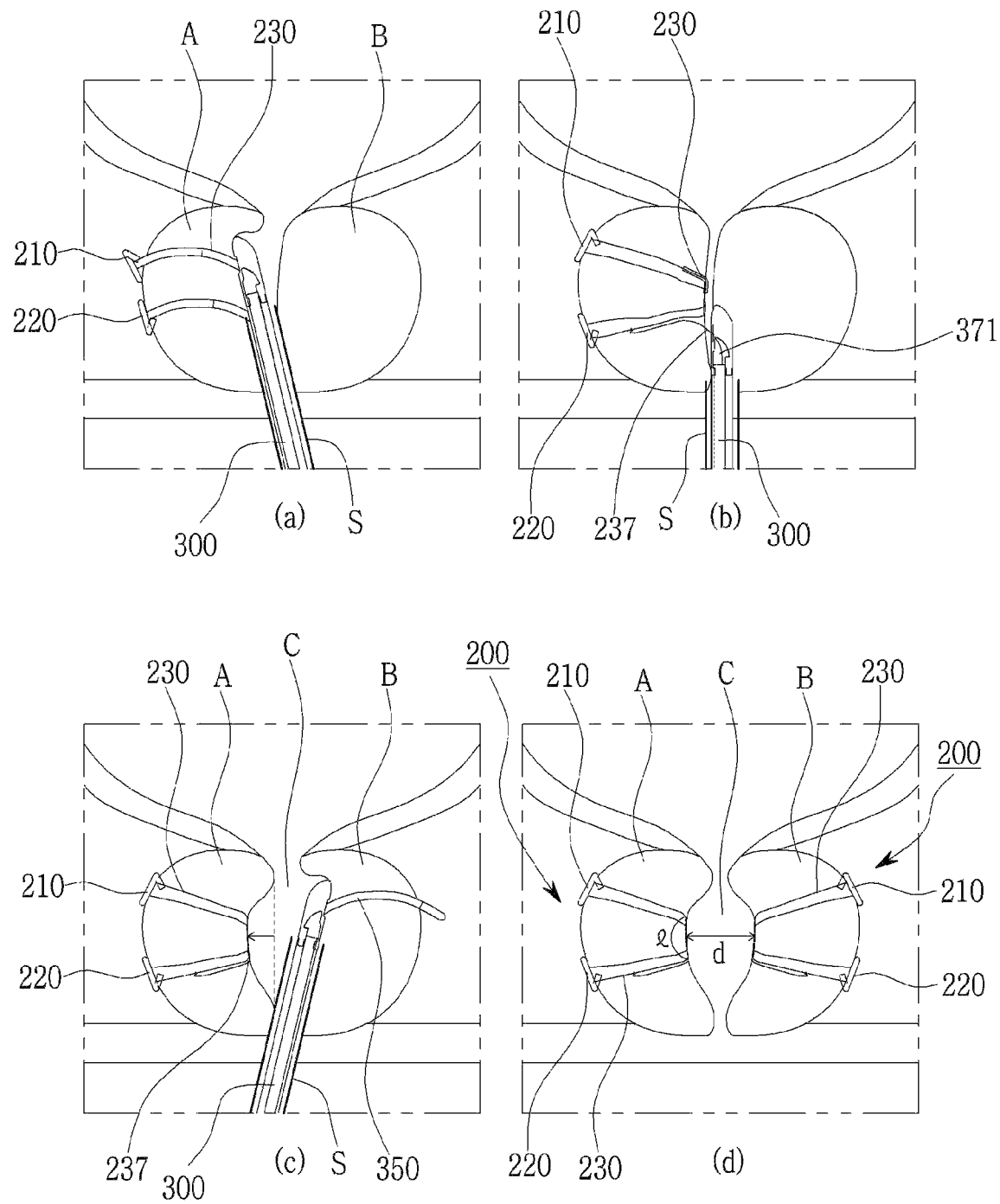

As shown in FIGS. 18 and 19, the operator inserts a transurethral endoscope 600 into the sheath 300 inserted into the urethra (C) through the outer sheath (S) in order to inspect the inside of the prostate gland, and manipulates the benign prostatic hyperplasia treatment device so that the needle 350 penetrates the prostate lobes A and B and a pair of the anchors 210 and 220 is arranged outside the prostate lobes A and B.

The sheath 300 is formed in a tubular shape with a predetermined length, and includes: a sheath body 300a formed by a needle insertion tube 310, an endoscope insertion tube 320 and a blade shaft movement tube 330 combined integrally; a needle guide member 340 disposed at the front end of the sheath body 300a to guide the needle 350 toward the prostate lobes A and B; the needle 350 accommodated in the needle insertion tube 310 to guide the anchor assembly 200 to the prostate lobes A and B; a pusher 360 inserted into the rear end of the anchor assembly 200 inside the needle 350 to push the anchor assembly 200 toward the front end of the needle; a needle blade part 370 disposed below the needle guide part 340 to be movable in the back-and-forth direction in order to cut the ligature 230; and a sheath fixing member 380 for joining the sheath 300 to the handle frame part 100.

The needle 350 is accommodated in the needle insertion tube 310, and the endoscope insertion tube 320 is disposed integrally with a lower portion of the needle insertion tube 310 to provide a passage through which the endoscope 600 moves. The blade shaft movement tube 330 is integrally combined with a lower portion of the endoscope insertion tube 320 to provide a passage through which a blade plate connecting shaft 373 moves.

The sheath body 300a is formed by a vertical combination of the needle insertion tube 310, the endoscope insertion tube 320 and the blade shaft movement tube 330 as shown in FIG. 4. The rear end of the sheath body 300a is inserted into a sheath insertion hole 411c of the needle holder 410. In this instance, as shown in FIG. 5, the endoscope insertion tube 320 is longer than the needle insertion tube 310 and the blade shaft movement tube 330, and an end portion 320a of the endoscope insertion tube 320 is arranged outside the needle holder 410.

Moreover, as shown in FIG. 6, the transurethral endoscope 600 is inserted into the end portion 320a of the endoscope insertion tube 320 and a transurethral endoscope inlet 610 is arranged at the end portion 320a.

The needle 350 is inserted into the rear end of the needle insertion tube 310, and the pusher 360 is assembled through the rear end. The needle guide member 340 is detachably combined with the front ends of the needle insertion tube 310 and the blade shaft movement tube 330.

Figure 1:
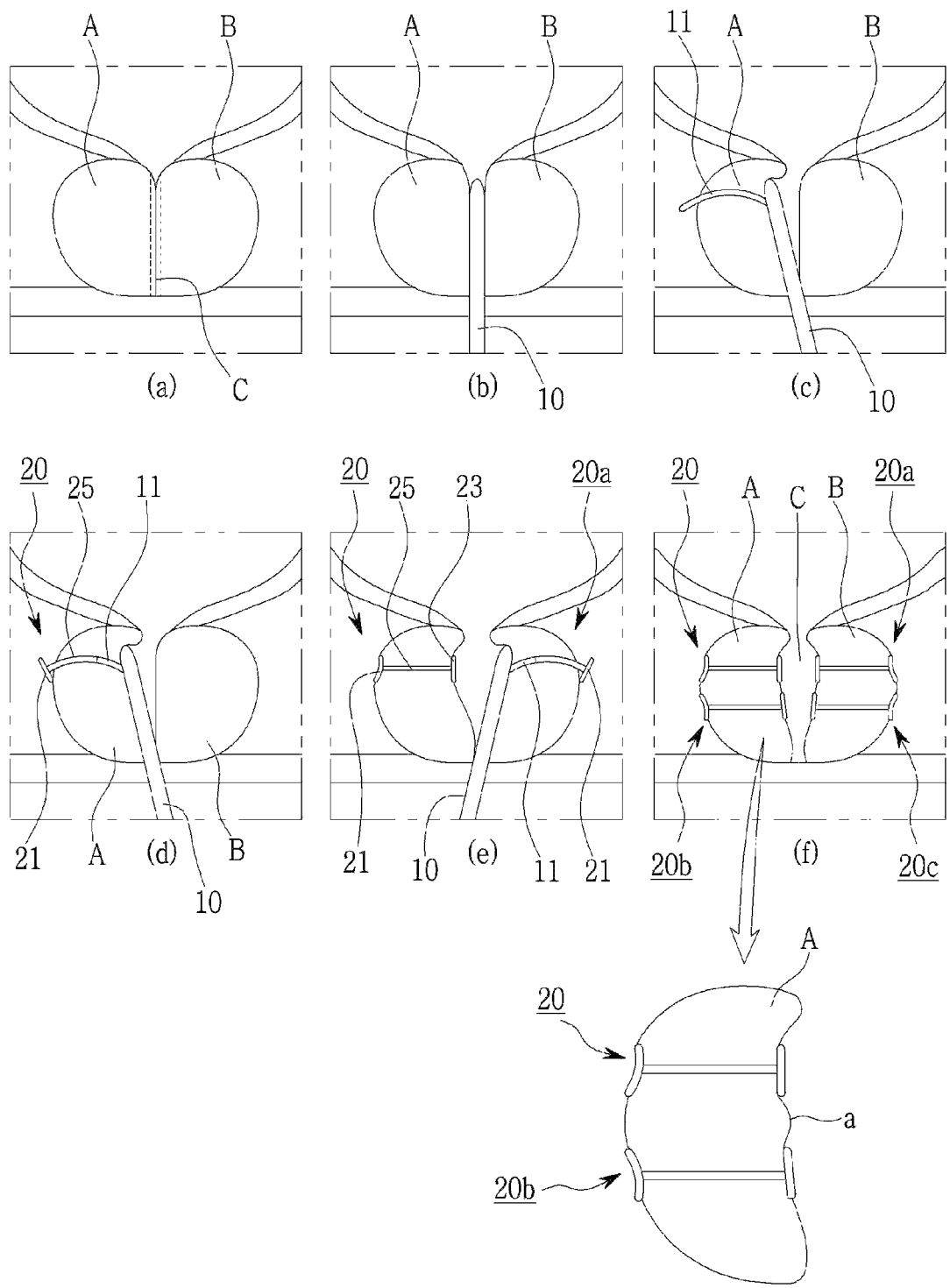
FIG. 1 is an exemplary view showing a conventional benign prostatic hyperplasia treatment method.

Here, as shown in FIG. 1, the components of the sheath 300, the handle frame part 100, the anchor assembly 200, the needle manipulating part 400, and the thread winder 500 are completely assembled and are sterilized and packaged by a manufacturing company to be provided to hospitals. Therefore, the benign prostatic hyperplasia treatment device according to the embodiment of the present invention is improved in user convenience since the operator can use it as it is without the need to disassemble or assemble the components during the surgical operation.

Figure 9:
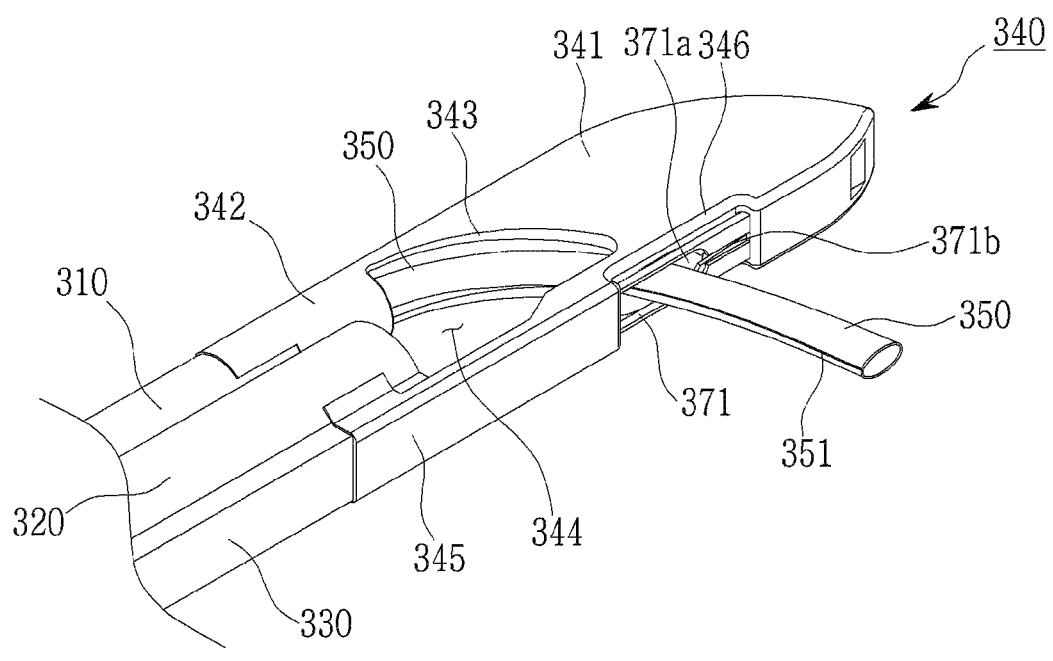
FIG. 9 is a view showing a structure of a needle guide member of the benign prostatic hyperplasia treatment device according to the embodiment of the present invention.
Figure 9:
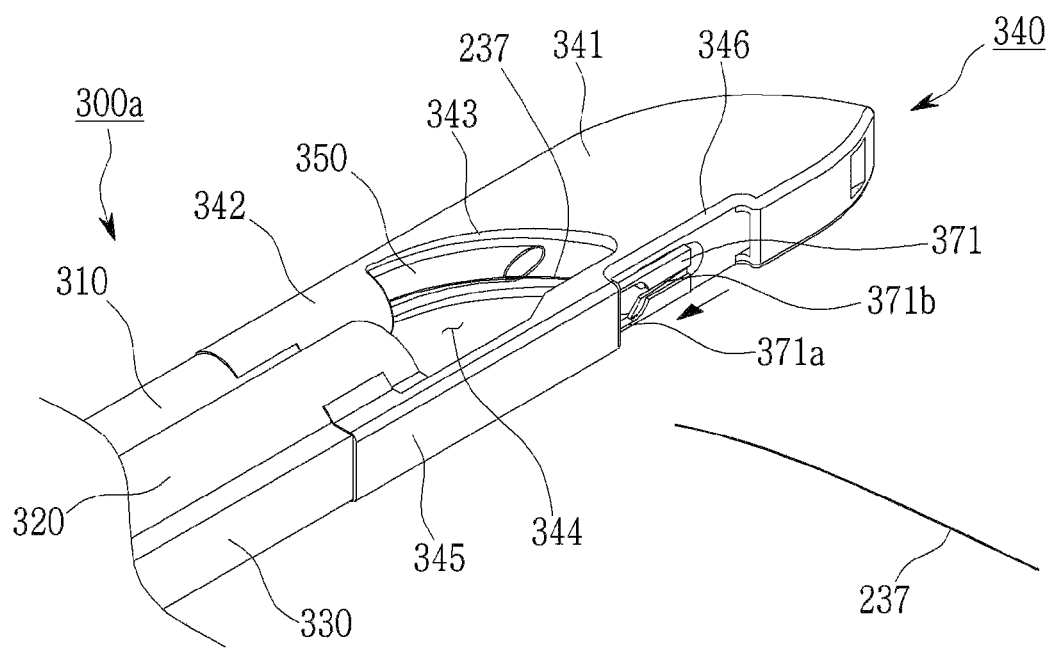

FIG. 9 is a view showing a front end structure of the sheath 300. As shown in FIG. 9(a), the needle guide member 340 includes a guide body 341, a needle insertion tube connecting tube 342 which protrudes rearwards from the guide body 341 and is combined with the needle insertion tube 310, and a blade shaft connecting tube 345 combined with the blade shaft movement tube 330.

The needle guide member 340 is fixed in position when the needle insertion tube connecting tube 342 and the blade shaft connecting tube 345 are respectively combined with the needle insertion tube 310 and the blade shaft movement tube 330. A needle exposure hole 344 for exposing the needle 350 externally is formed between the needle insertion tube connecting tube 342 and the blade shaft connecting tube 345. The transurethral endoscope 600 moved into the endoscope insertion tube 320 may be exposed into the urethra (C) through the needle exposure hole 344.

Furthermore, the ligature 230 accommodated in the needle 350 is exposed externally through the needle exposure hole 344, and the ligature 230 can be moved to the prostate lobes A and B without interruption.

A needle outlet 346 for discharging the needle 350 externally is formed at an upper portion of the blade shaft connecting tube 345. A blade plate 371 of the needle blade part 370 is joined to the needle outlet 346 to be slidably movable.

A needle guide curved surface 343 for guiding the needle 350 to the urethra (C) is formed on the inner wall of the upper portion at which the needle exposure hole 344 is formed. The needle 350 is arranged inside the needle insertion tube 310 in an initial state as shown in FIG. 9(b). When the operator manipulates the needle trigger 420, as shown in FIG. 9(a), the needle 350 is extended externally to a predetermined length through the needle guide member 340.

In this instance, the needle 350 is bent at a predetermined angle along the curved surface of the needle guide curved surface 343 and penetrates the prostate lobes A and B.

The needle 350 has a predetermined length, is inserted into the needle insertion tube 310, and is guided into the prostate lobes A and B through the needle guide member 340 when the operator manipulates the needle trigger 420.

The needle 350 may be made of metal or metal alloy, preferably, nitinol. The needle 350 is manufactured to be curved at the front end. The needle 350 is located on the needle guide curved surface 420 when being accommodated in the needle insertion tube 310, so as to elastically maintain the curved form corresponding to the curvature of the needle guide curved surface 343. When the needle is deployed by the needle trigger 420 and is deployed into the prostate lobes A and B through the needle guide member 340, the needle 350 is adjusted in terms of its deployment angle by the needle guide curved surface 343 and is curved to match the curvature formed when being manufactured.

As shown in the enlarged view of FIG. 6, a needle slot 351 for exposing the ligature 230 of the anchor assembly 200 externally is formed at the front end of the needle 350 deployed through the needle outlet 346. The length of the needle slot 351 is set to be equal to or less than the sum of lengths of the first anchor 210 and the second anchor 220. In one instance, if the first anchor 210 and the second anchor 220 are 8 mm in length, the needle slot 351 is 16 mm in length and 0.4 mm in width. In this instance, the needle slot 351 can get inwardly narrower from the front end.

The pusher 360 is arranged at the rear end of the needle 350, pushes the first anchor 210 and the second anchor 220 in consecutive order when the needle 350 penetrates the tissues of the prostate lobes A and B, so that the first anchor 210 and the second anchor 220 are released from the needle 350.

As shown in FIG. 5, the pusher 360 includes: a pusher shaft 361 inserted into the needle 350; a pusher holder 363 formed at the rear end of the pusher shaft 361 to a predetermined length and inserted into the needle holder 410; a pusher button shaft 365 extending at right angles to the rear end of the pusher shaft 361; a pusher button 366 formed at an end portion of the pusher button shaft 365 to occupy a predetermined area and manipulated by the operator; and a pusher tail 367 protruding upwards at the front end of the pusher shaft 361 to fix the position of the pusher shaft 361.

The pusher shaft 361 is inserted into the needle 350, and is located at the rear end of the second anchor 229 as shown in the enlarged view of FIG. 6. The pusher shaft 361 pushes the second anchor 220 to push the first anchor 210 and the second anchor 220 out of the needle 350 when the operator moves the pusher shaft 361 forwards using the pusher button 366.

The pusher holder 363 is accommodated between a horizontal bar 411 of the needle holder 410 and an upper combining bar 415. The pusher holder 363 extends from the rear end of the pusher shaft 361 to a predetermined length to support back-and-forth movement of the pusher shaft 361.

The pusher button shaft 365 extends from a boundary area of the pusher shaft 361 and the pusher holder 363 to pusher movement slits 112 and 121 of the left frame 110 and the right frame 120. The pusher button 366 is joined to an end portion of the pusher button shaft 365 extended out of the left and right pusher movement slits 112 and 121.

As shown in FIG. 2, the operator presses the pusher button 366, which is extended out of the pusher movement slits 112 and 121 of the handle frame part 100, in the back-and-forth direction in order to adjust the position of the pusher shaft 361.

Figure 10:
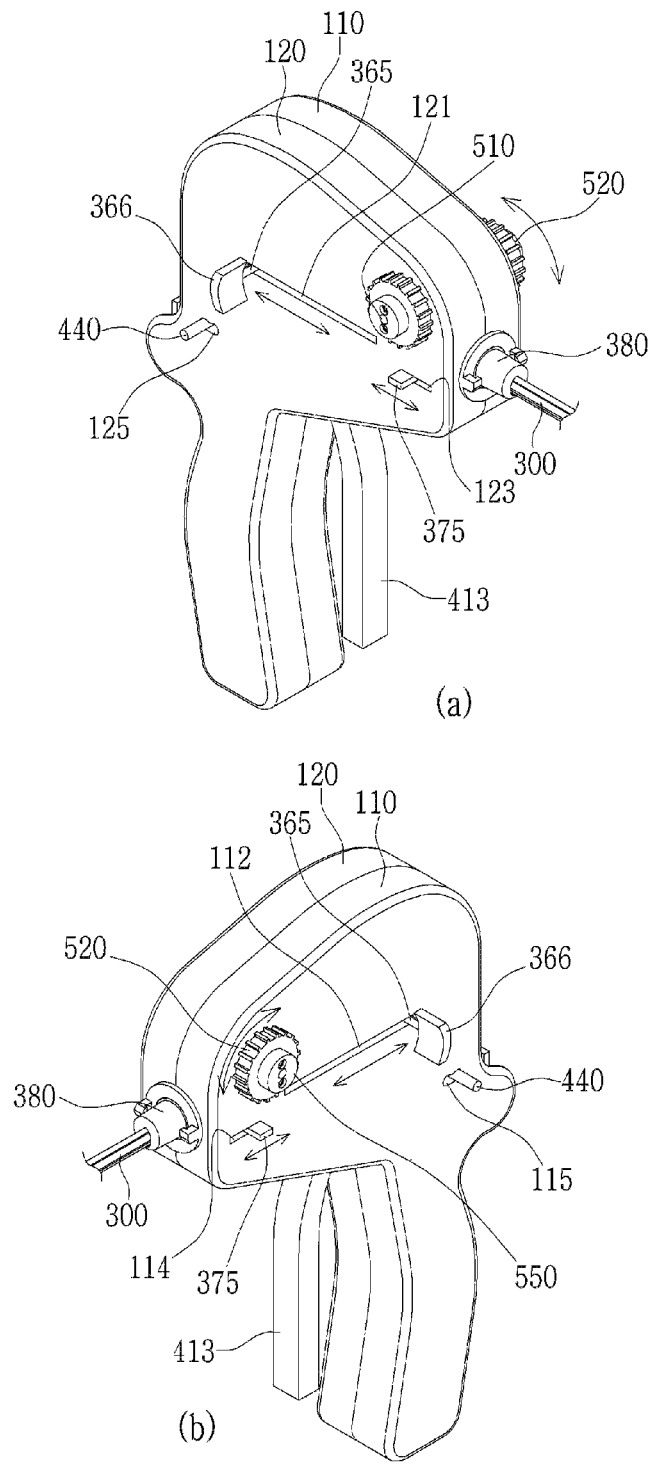
FIG. 10 is a perspective view showing an external structure of a handle frame part of the benign prostatic hyperplasia treatment device according to the embodiment of the present invention.

As shown in FIG. 10(a), when the pusher button 366 is located at the rearmost end of the pusher movement slits 112 and 121, the pusher shaft 361 is pushed back and the first anchor 210 and the second anchor 220 are all accommodated in the needle 350 as shown in FIG. 16(a).

Figure 15:
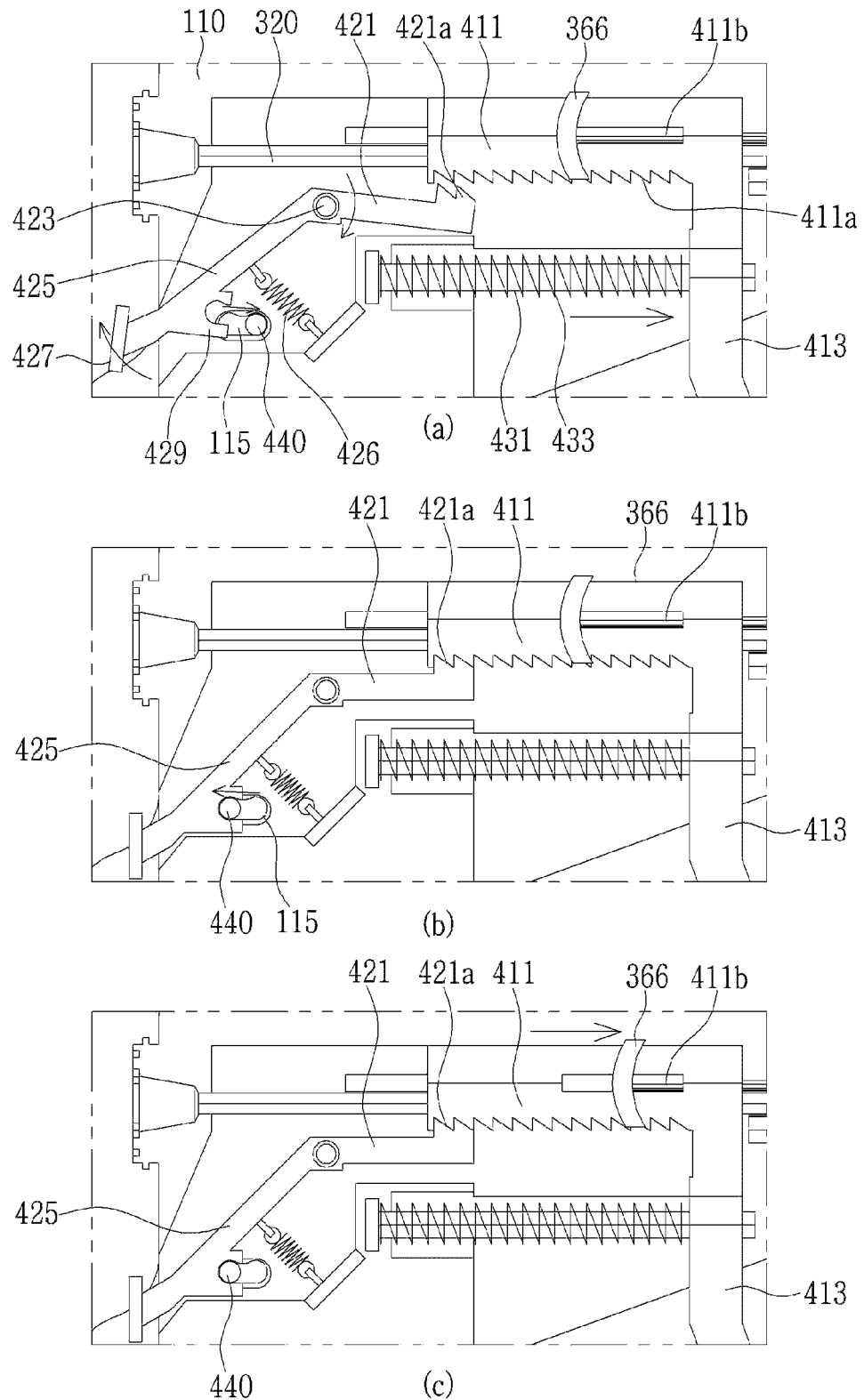
FIGS. 15 to 17 are exemplary views showing a use process of the benign prostatic hyperplasia treatment device according to the embodiment of the present invention.

As shown in FIG. 15(c), when the operator pushes the pusher button 366 forwards, the pusher shaft 361 pushes the second anchor 220 as much as the pusher button is moved so as to push the first anchor 210 out of the needle 350 as shown in FIG. 16(b).

Here, the pusher tail 367 limits the displacement of the pusher button 366 moved by the operator to be as long as the length of the anchors 210 and 220.

FIG. 11(b) is a perspective view showing a combination structure of the needle holder 410 and the pusher 360. A tail position fixing rail 416 is formed on the upper surface inside the upper combining bar 415 of the needle holder 410 to correspond to the length of the needle slot 351. Additionally, a first groove 416a, a second groove 416b and a third groove 416c are formed to be upwardly hollow and are spaced apart from one another at intervals corresponding to the length of the anchors 210 and 220.

When the operator moves the pusher button 366, the pusher tail 367 is caught and joined to the first groove 416a, the second groove 416b and the third groove 416c in consecutive order, and limits the displacement of the pusher shaft 361 by the length of the anchors 210 and 220.

Figure 17:
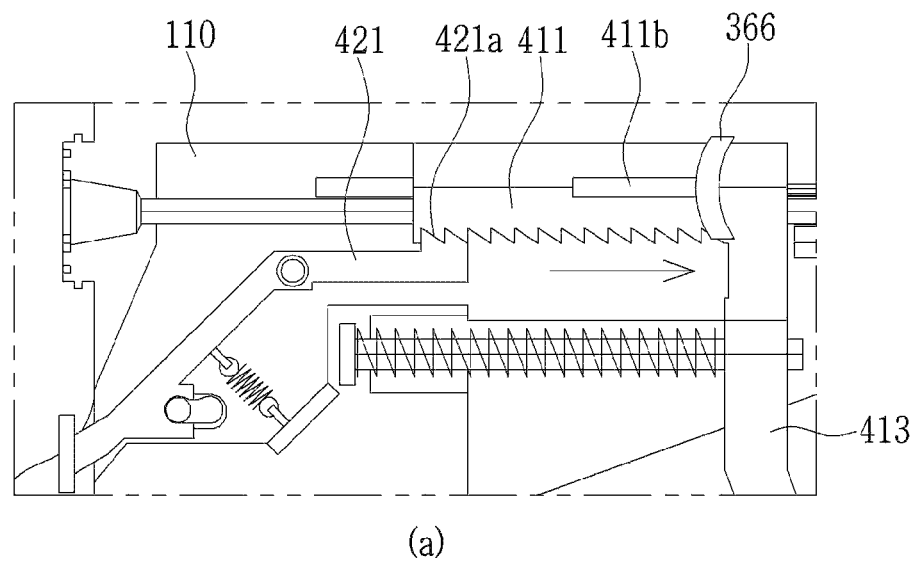
Figure 17:
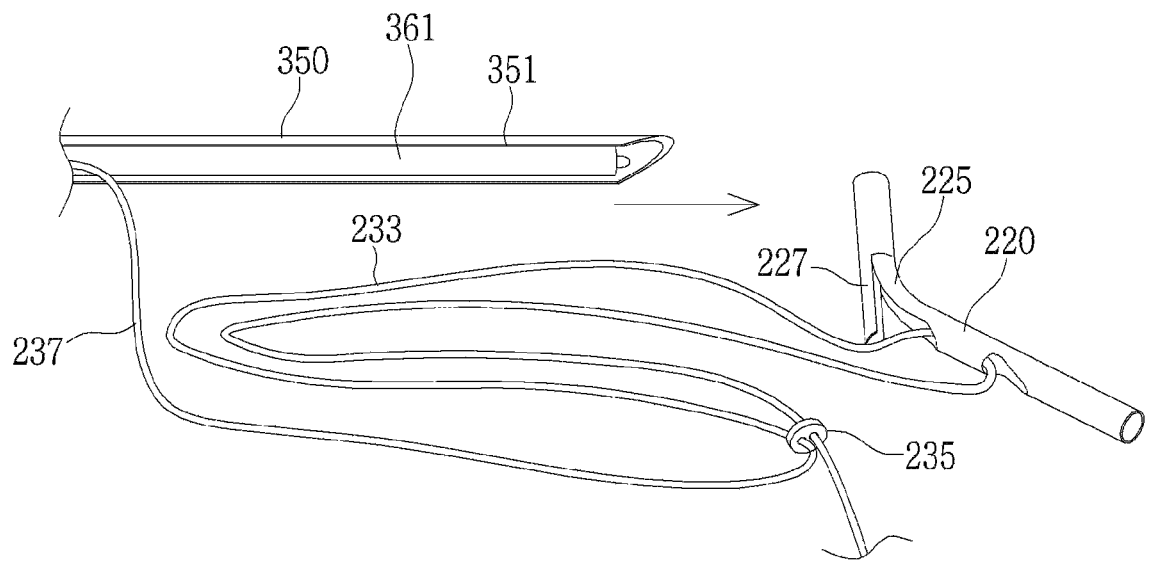

Therefore, when the pusher tail 367 is located at the first groove 416a, the first anchor 210 and the second anchor 220 are all accommodated in the needle 350. When the operator presses the pusher button 366 to move the pusher shaft 361 forwards so that the pusher tail 367 is located at the second groove 416b, the first anchor 210 is pushed out of the needle 350. Moreover, when the operator moves the pusher shaft 361 forwards so that the pusher tail 367 located at the second groove 416b is now located at the third groove 416c, as shown in FIG. 17, the pusher shaft 361 is moved to the front end of the needle 350 and the second anchor 220 is pushed out of the needle 350.

When the first anchor 210 and the second anchor 220 are deployed and arranged on the outer surfaces of the prostate lobes A and B, the needle blade part 370 serves to cut the free end 237 of the ligature 230 that has been adjusted in length.

As shown in FIG. 5, the needle blade part 370 includes: the blade plate 371 slidably joined to the needle outlet 346 of the needle guide member 340; a blade plate connecting shaft 373 extending from the blade plate 371 to the handle frame part 100; and a blade pressing button 375 disposed at the rear end of the blade plate connecting shaft 373.

The blade plate 371 is disposed at the needle outlet 346, is moved back and forth by the blade plate connecting shaft 373, and cuts the free end 237 of the ligature 230.

As shown in FIG. 19(b), when the first anchor 210 and the second anchor 220 released from the needle 350 are located on the outer surface of the prostate gland, the free end 237 of the ligature 230 is connected to the thread winder 500 of the handle frame part 100 through the needle insertion tube 310. The free end 237 extends through the needle insertion tube 310 in the space next to the needle 350 and is connected to the thread winder 500.

The operator rotates the winder handle 520 of the thread winder 500 to wind the free end 237, and shortens the length-adjustable loop 233 of the ligature 230 surrounding the prostate lobes A and B. In this instance, the blade plate 371 is moved and cuts the ligature 230 that has been adjusted in length.

As shown in the enlarged view of FIG. 5, the blade plate 371 is formed in a plate shape with an area which is slidably movable in the needle outlet 346. A needle discharge hole 371a for discharging the needle 350 is formed inside the blade plate 371. Moreover, a blade slit 371b is formed at an upper portion of the needle discharge hole 371a.

The blade slit 371b is formed to get narrower, and inner end portions which face each other are formed to be sharp.

As shown in FIG. 9(b), when the operator pulls the blade plate connecting shaft 373 backwards, the blade plate 371 slides backwards, and the ligature 230 is inserted into the blade slit 371b. Then, the blade slit 371b, which is narrow and sharp, and the ligature 230 come into contact, and the free end 237 of the ligature 230 is cut.

The blade plate connecting shaft 373 extends to the blade button movement slits 114 and 123 of the handle frame part 100 through the blade shaft movement tube 330. The blade plate connecting shaft 373 transfers the back-and-forth movement of the blade pressing button 375 by the operator to the blade plate 371.

The blade pressing button 375 protrudes externally from the left and right blade button movement slits 114 and 123 of the handle frame part 100 and is moved back and forth by the operator.

Before the anchors 210 and 220 are released from the needle 350, as shown in FIG. 2, the blade pressing button 375 is located at the front of the blade button movement slits 114 and 123. On the other hand, in order to cut the free end 237 of the ligature 230 after the first anchor 210 and the second anchor 220 are all located on the prostate lobes A and B, the operator moves the blade pressing button 375 to the back of the blade button movement slits 114 and 123 as shown in FIG. 10(a).

Therefore, as shown in FIG. 9(b), the blade plate 371 is pulled backwards and cuts the ligature 230.

The blade plate 371 is accommodated in the needle guide member 340, and the blade plate connecting shaft 373 is connected to the blade pressing button 375 and is combined with the handle frame part 100.

The sheath fixing member 380 combines the sheath 300 with the handle frame part 100. As shown in FIG. 4, the sheath fixing member 380 includes: a sheath combining plate 381 forcibly inserted into a sheath combining plate insertion groove 119 of the handle frame part 100; a sheath combining tube 383 into which the sheath 300 is inserted; and a fixing ring 385 fixed between the sheath combining tube 383 and the sheath combining plate 381.

The sheath combining plate 381 is fixed in position by being inserted into the sheath combining plate insertion groove 119 of the handle frame part 100. A plurality of combining protrusions 381a are formed on the front surface of the sheath combining plate 381. The sheath 300 is inserted into the sheath combining tube 383. A plurality of protrusion insertion holes (not shown) into which the combining protrusions 381a are inserted are formed in the rear surface of the sheath combining tube 383.

The sheath 300 penetrates through the sheath combining tube 383 and the sheath combining plate 381 in consecutive order, and is inserted into the sheath insertion hole 411c of the needle holder 410. The sheath combining tube 383 is fixed in position by being joined to the combining protrusions 381a of the sheath combining plate 381.

The fixing ring 385 is fixed between the sheath combining tube 383 and the sheath combining plate 381. As shown in FIG. 18, during the surgical operation, the fixing ring 385 is used to fix the outer sheath (S) on the outer face of the sheath body 300a.

The outer sheath (S) is fixed to the outer face of the sheath body 300a by being caught and joined to a locking hook 385a of the fixing ring 385.

The needle manipulating part 400 adjusts the positions of the needle 350 and the anchor assembly 200 in steps so that the needle 350 is deployed out of the sheath 300 and the anchor assembly 200 is released from the needle 350 and is arranged in the prostate lobes A and B.

As shown in FIGS. 4 and 5, the needle manipulating part 400 includes: the needle holder 410 for adjusting the position of the needle 350; the needle trigger 420 for discharging the needle 350 out of the needle guide member 340 by elastically firing the needle holder 410; an elastic holder support part 430 for providing elastic force to deploy the needle holder 410 by the user's manipulation of the needle trigger 420; and a trigger locking member 440 for locking the needle trigger 420.

The needle holder 410 is moved forwards by the needle trigger 420 and the elastic holder support part 430, and the needle 350 is deployed through the needle guide member 340 and penetrates the prostate lobes A and B. The needle holder 410 includes: the horizontal bar 411 formed horizontally; the pulling lever 413 extending downwards from the front end of the horizontal bar 411 to a predetermined length and pressed by the operator; and the upper combining bar 415 combined with the upper portion of the horizontal bar 411 in the state where the needle 350 is fixed.

The endoscope insertion tube 320 of the sheath 300 is accommodated in the horizontal bar 411. Holder position adjusting teeth 411a are formed at a lower portion of the horizontal bar 411 in a longitudinal direction. The holder position adjusting teeth 411a engage with holder position fixing teeth 421a of the needle trigger 420 so as to adjust the position of the needle holder 410 inside the handle frame part 100. A pusher button movement rail 411b of a predetermined length is formed on the upper portion of the horizontal bar, and the sheath insertion hole 411c into which the sheath 300 is inserted is formed at the front of the horizontal bar 411.

The pulling lever 413 extends downwards from the horizontal bar 411 to a predetermined length, and as shown in FIG. 2, is extended out of the handle frame part 100. When the operator pulls the exposed pulling lever 413 with the hand, the needle holder 410 that has been moved forwards by the operator's manipulation of the needle trigger 420 adjusts its position to be returned to the back.

As shown in FIG. 4, a support shaft insertion hole 413a into which an elastic member support shaft 431 of the elastic holder support part 430 is inserted is formed at the front of the pulling lever 413. Therefore, the pulling lever 413 moves back and forth along the elastic member support shaft 431.

The upper combining bar 415 is combined with the upper portion of the horizontal bar 411 to form the pusher button movement rail 411b. The pusher button movement rail 411b is formed at a location corresponding to the left and right pusher movement slits 112 and 121 of the handle frame part 100, and the pusher button shaft 365 is accommodated therein to be movable.

The tail position fixing rail 416 described above is formed inside the upper combining bar 415 to adjust the displacement of the pusher 360.

The needle trigger 420 fixes the needle holder 410 in place or releases the fixed state of the needle holder 410 so that the needle holder 410 can be deployed forwards by elastic force of the elastic holder support part 430.

Figure 12:
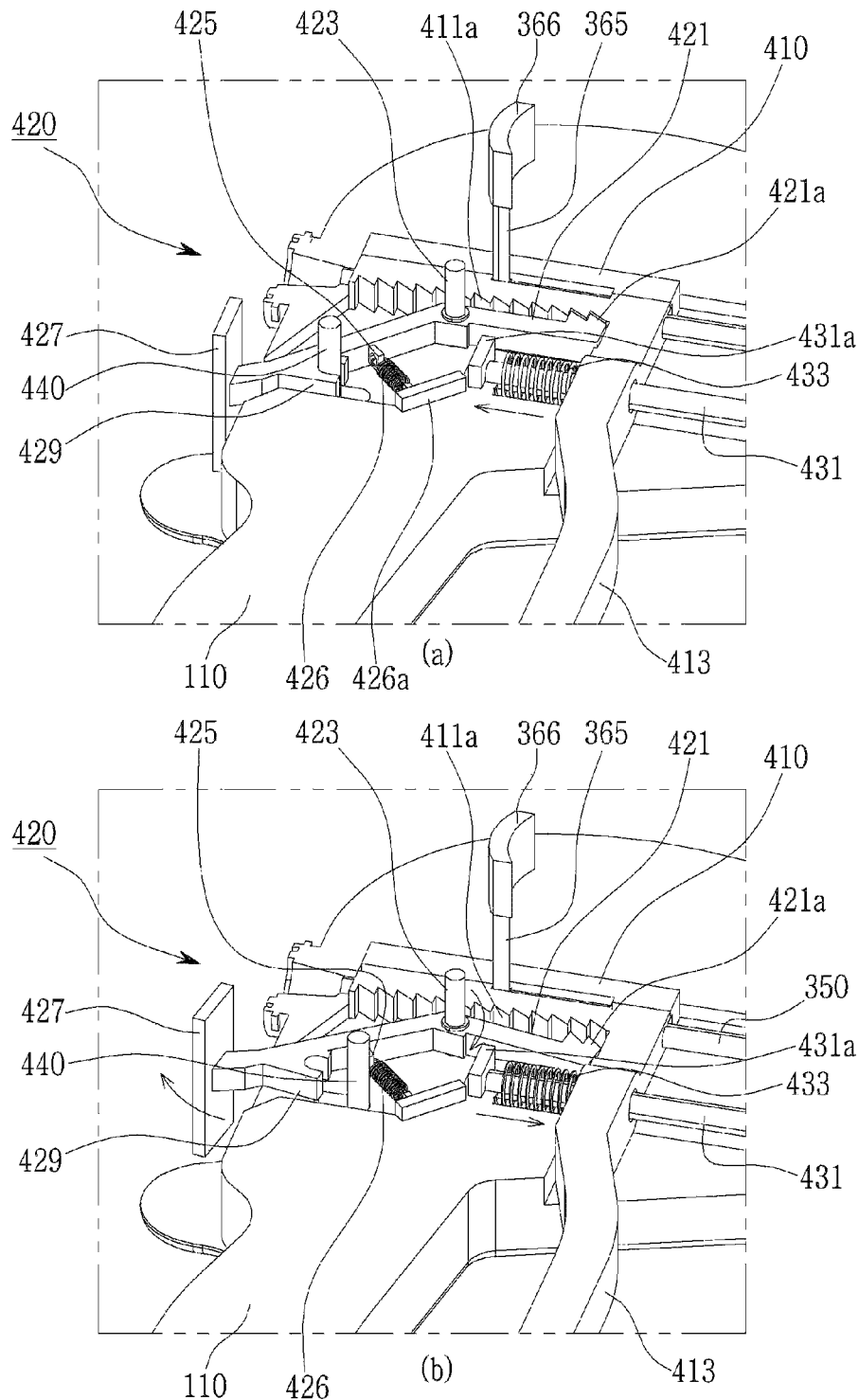
FIG. 12 is an exemplary view showing a manipulation process of a needle trigger of the benign prostatic hyperplasia treatment device according to the embodiment of the present invention.

As shown in FIGS. 5 and 12, the needle trigger 420 includes: a holder removable bar 421 attached to or detached from the needle holder 410; a frame support bar 425 formed at a lower portion of the holder removable bar 421 to be inclined; a trigger rotating shaft 423 combined with the movement handle frame part 100 so that the needle trigger 420 can be rotated; and a trigger return spring 426 providing elastic force so that the trigger rotating shaft 423 is rotated in the direction that the holder removable bar 421 is combined with the needle holder 410.

The holder removable bar 421, with a pivot at the trigger rotating shaft 423, is formed to be aligned with the horizontal bar 411 of the needle holder 410, and the holder position fixing teeth 421a is formed on the upper surface of the front end. As shown in FIG. 12(a), the holder position fixing teeth 421a engage with the holder position adjusting teeth 411a of the needle holder 410 to fix the position of the needle holder 410.

As shown in FIG. 12(b), when the needle trigger 420 is rotated about the trigger rotating shaft 423, the holder position fixing teeth 421a is separated from the holder position adjusting teeth 411a so that it is no longer attached to the needle holder 410. Therefore, the needle holder 410 is deployed forwards by elastic force of the elastic member 433 of the elastic holder support part 430 and is moved.

The frame support bar 425 is combined with the trigger return spring 426, so that elastic force of the trigger return spring 426 is transferred to the trigger rotating shaft 423 and the holder removable bar 421. The trigger return spring 426 has one end fixed to the frame support bar 425 and the other end combined with a frame fixing member 426a.

The trigger return spring 426 provides elastic force so that the trigger rotating shaft 423 is rotated in the direction that the holder removable bar 421 is fixed with the needle holder 410.

A trigger manipulation button 427 with a predetermined area is formed at the rear end of the frame support bar 425. As shown in FIG. 2, the trigger manipulation button 427 is extended out of the rear end of the handle frame part 100 and is pressed by the operator. When the operator presses the trigger manipulation button 427 upwards, the holder removable bar 421 is rotated as shown in FIG. 12(b), the holder position fixing teeth 421a is separated from the holder position adjusting teeth 411a, and the needle holder 410 is moved forwards.

A locking shaft receiving ring 429 is formed between the frame removable bar 425 and the trigger manipulation button 427. The locking shaft receiving ring 429 has an open end and the trigger locking member 440 is accommodated therein.

As shown in FIG. 12(a), when the trigger locking member 440 is accommodated in the locking shaft receiving ring 429, rotation of the needle trigger 420 is limited. Therefore, the needle holder 410 can remain fixed in position.

On the other hand, as shown in FIG. 12(b), when the trigger locking member 440 is separated from the locking shaft receiving ring 429, the operator can manipulate the trigger manipulation button 427 to rotate the needle trigger 420.

The trigger locking member 440 is disposed to be movable horizontally along the locking member movement grooves 115 and 125 of the handle frame part 100. In this instance, the positions of the rear ends of the movement grooves 115 and 125 are formed to correspond to the position of the locking shaft receiving ring 429 of the needle trigger 420.

Therefore, as shown in FIG. 15(b), as soon as the trigger locking member 440 is located at the back of the movement grooves 115 and 125, the trigger locking member 440 is accommodated in the locking shaft receiving ring 429. On the other hand, as shown in FIG. 15(a), when the trigger locking member 440 is located at the front of the movement grooves 115 and 125, the trigger locking member 440 gets out of the locking shaft receiving ring 429.

The elastic holder support part 430 causes the needle holder 410 to be deployed forwards at a rapid speed and provides force for the needle 350 accommodated in the needle insertion tube 310 to be deployed through the needle outlet 346 of the needle guide member 340 and penetrate the prostate lobes A and B.

Figure 11:
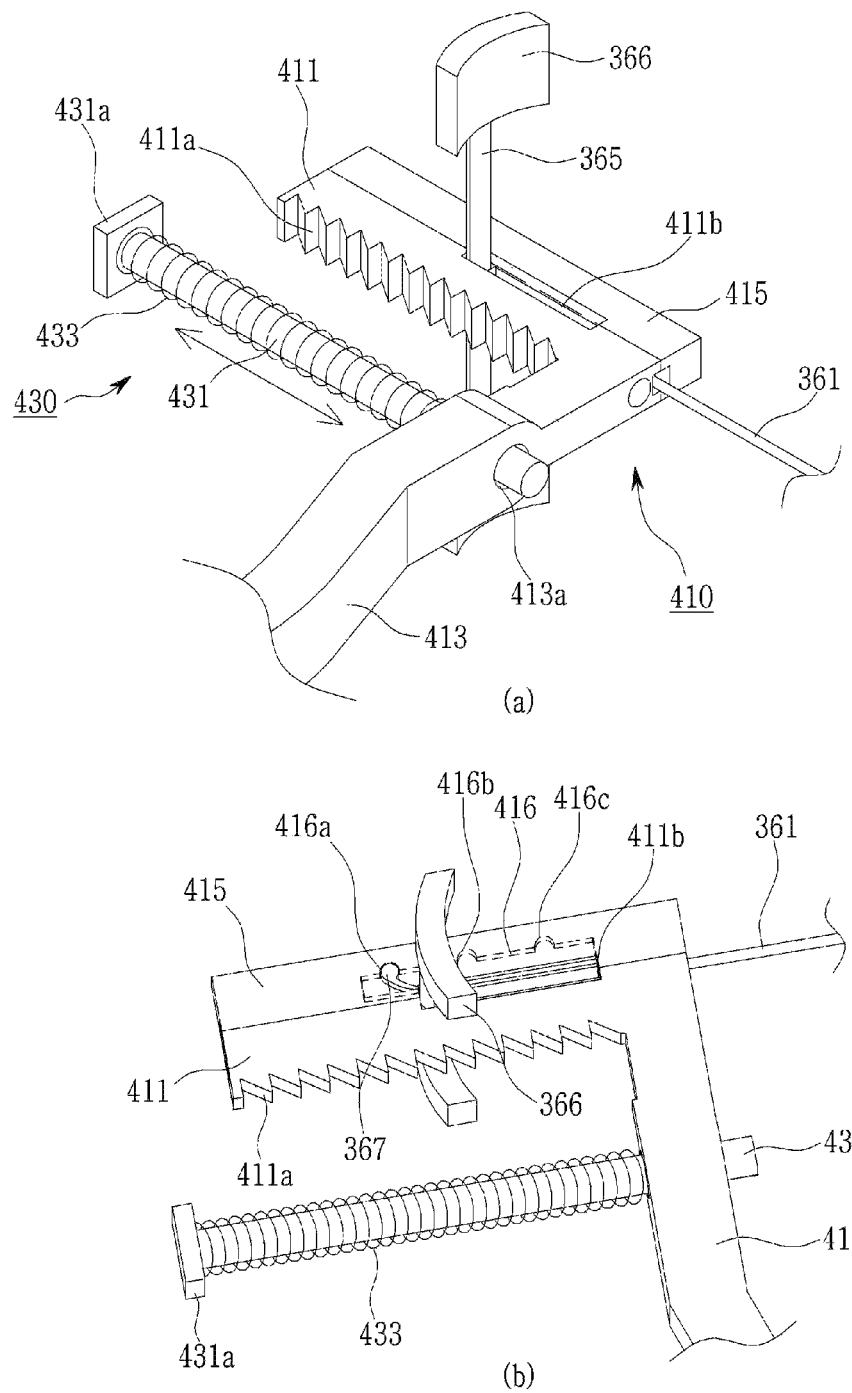
FIG. 11 is a perspective view showing a structure of a needle manipulating part of the benign prostatic hyperplasia treatment device according to the embodiment of the present invention.

As shown in FIG. 11, the elastic holder support part 430 includes: an elastic member support shaft 431 combined with the pulling lever 413 in a widthwise direction; and the elastic member 433 combined with the elastic member support shaft 431. One end of the elastic member support shaft 431 is accommodated in the support shaft insertion hole 413a of the pulling lever 413, and a shaft fixing plate 431a which is fixed at the handle frame part 100 is disposed at the other end of the elastic member support shaft 431.

The elastic member 433 is disposed between the pulling lever 413 and the shaft fixing plate 431a to provide elastic force so that the needle holder 410 can be moved back and forth.

As shown in FIG. 12(a), when the operator pulls the pulling lever 413 backwards and combines the holder position fixing teeth 421a of the holder removable bar 421 of the needle trigger 420 with the front of the holder position adjusting teeth 411a, the elastic member 433 is compressed between the pulling lever 413 and the shaft fixing plate 431a.

As shown in FIG. 12(b), when the operator moves the trigger locking member 440 from the locking shaft receiving ring 429, the holder position fixing teeth 421a are free from the holder position adjusting teeth 411a, and the elastic member 433 provides elastic force to return to the initial position so that the needle holder 410 moves forwards along the elastic member support shaft 431.

As shown in FIG. 6, the needle 350 inside the needle insertion tube 310 is deployed through the needle outlet 346 of the needle guide member 340 and penetrates the prostate gland due to the speed of the needle holder 410 moving forwards.

In this instance, the length by which the needle 350 is deployed through the needle outlet 346 of the needle guide member 340 by elastic force of the elastic member 433 is such that the needle 350 extends from the urethra (C) into the tissue of one prostate lobe A and comes out of its outer surface.

The thread winder 500 winds the free end 237 of the ligature 230 extending to the handle frame part 100 through the needle insertion tube 310 and adjusts the length of the length-adjustable loop 233 so as to adjust the intensity with which the anchor assembly 200 compresses the prostate lobes A and B.

As shown in FIG. 4, the thread winder 500 is combined with the inside and the outside of thread winder receiving recess 113 of the handle frame part 100.

Figure 13:
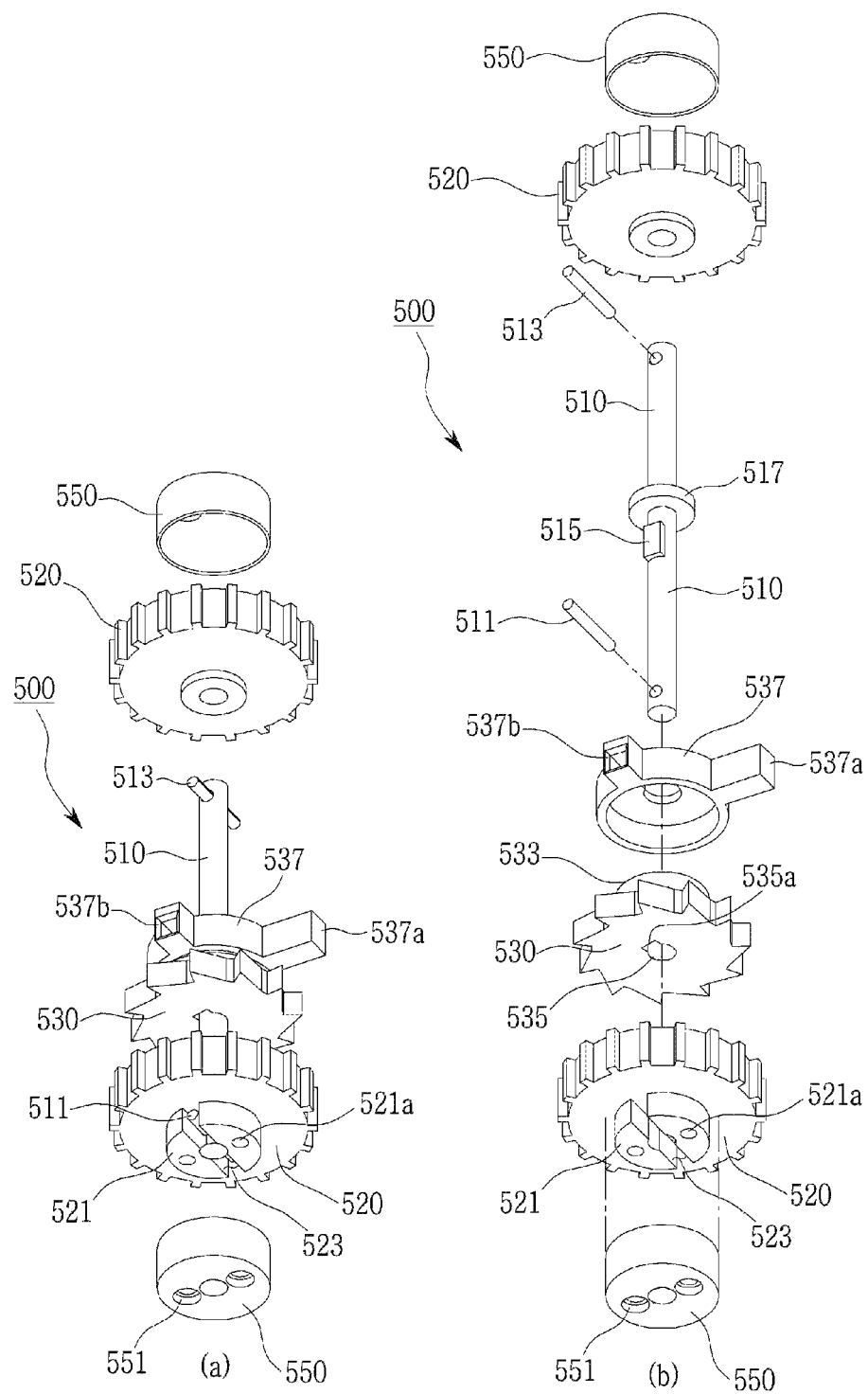
FIG. 13 is a view showing a structure of a thread winder of the benign prostatic hyperplasia treatment device according to the embodiment of the present invention.
Figure 14:
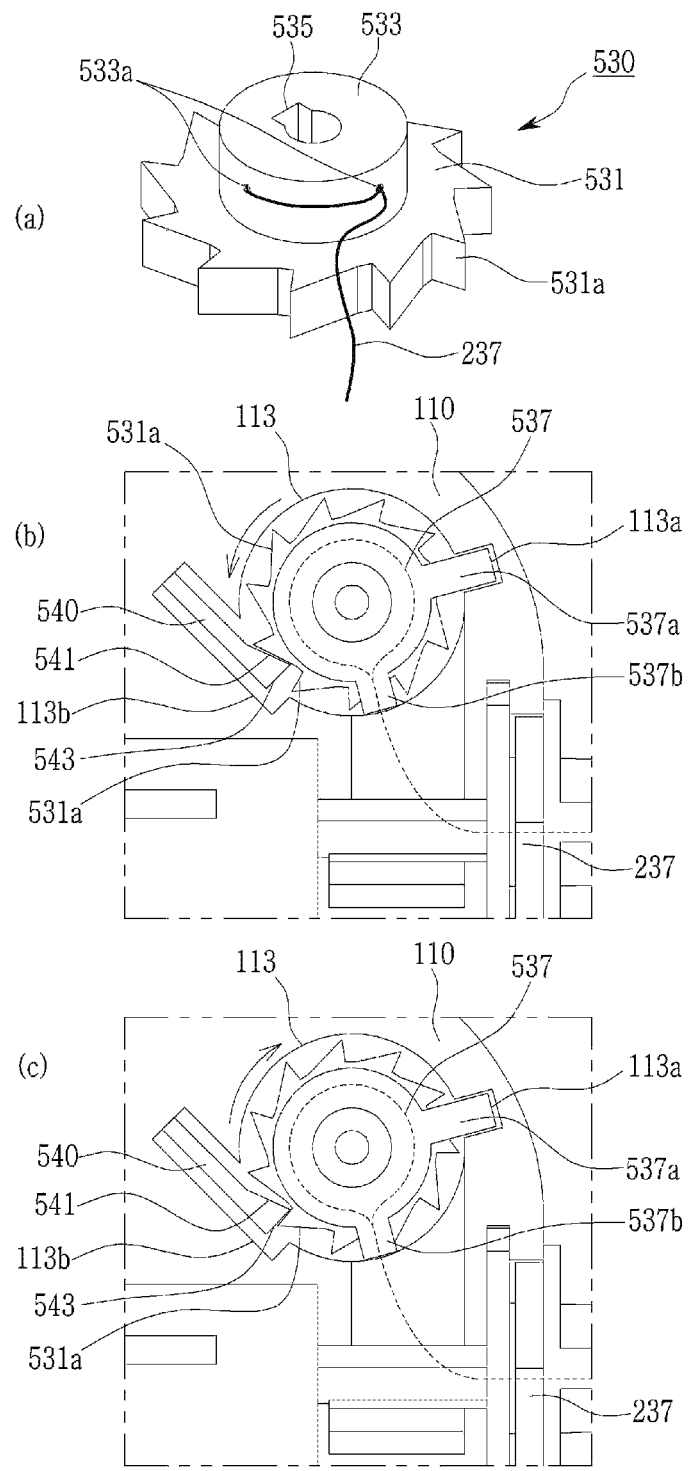
FIG. 14 is an exemplary view showing an operation of a winder gear of the thread winder of the benign prostatic hyperplasia treatment device according to the embodiment of the present invention.

FIG. 13 is a view showing a structure of the thread winder 500, and FIG. 14 is an exemplary view showing an operational process of the thread winder 500.

As shown in the drawings, the thread winder 500 includes: the winder shaft 510; the winder handle 520 combined with one side of the winder shaft 510 and rotated by the operator; the winder gear 530 combined with the other side of the winder shaft 510 and rotating together with the winder shaft 510 so that the free end 237 is wound on the outer circumferential surface thereof; the thread guide cap 537 for covering the outer surface of the winder gear 530 and guiding the free end 237 to the winder gear 530; the one-way rotation limit bar 540 for limiting the rotational direction so that the winder gear 530 can rotate just in one direction; and a winder handle cover 550 combined with the winder handle 520.

As shown in FIGS. 10(a) and 10(b), the winder shaft 510 penetrates through the handle frame part 100 to be combined with the handle frame part 100, and is rotated by the winder handle 520. The winder shaft 510 is fixed to the winder handle 520 and the winder gear 530, and is rotated together with the winder gear 530 accommodated in the handle frame part 100 when the operator rotates the winder handle 520.

As shown in FIG. 13(b), a first holder bar 511 and a second holder bar 513 are respectively combined with the lower end and the upper end of the winder shaft 510. The first holder bar 511 and the second holder bar 513 are combined with the winder shaft 510 in the horizontal direction. The first holder bar 511 is inserted into a holder combining groove 523 of a holder combining wheel 521.

The first holder bar 511 is combined with the holder combining wheel 521 so that rotation of the winder handle 520 is transferred to the winder shaft 510.

The winder handle 520 and the winder handle cover 550 are combined with the second holder bar 513 in the same way as the first holder bar 511. The operator manipulates any one of a pair of the winder handles 520 to adjust the length of the free end 237.

A protruding key 515 is disposed on the winder shaft 510. The key 515 fits inside a key hole 535a formed in a shaft insertion hole 535 of the winder gear 530. Therefore, rotation of the winder shaft 510 is transferred to the winder gear 530.

As shown in FIG. 10(b), the winder handle 520 is combined with the outer face of the right frame 120 so that the operator can rotate it. The holder combining wheel 521 is disposed on the outer face of the winder handle 520 to protrude out. An internal combining member insertion hole 521a is formed in the surface of the holder combining wheel 521 so that a fastening member (not shown) for fastening the holder combining wheel 521 and the winder handle cover 550 is inserted therein. The fastening member (not shown) is inserted into the internal combining member insertion hole 521a through an external combining member insertion hole 551 of the winder handle cover 550 so that the winder handle cover 550 covers the outer face of the holder combining wheel 521.

The holder combining groove 523 is formed in the middle area of the holder combining wheel 521 widthwise. The first holder bar 511 of the winder shaft 510 is inserted into the holder combining groove 523.

The winder gear 530 is accommodated in the thread winder receiving recess 113 of the left frame 110 in the state where the winder gear 530 is combined with the winder shaft 510. The winder gear 530 is formed by a vertical stacking of a one-way rotation wheel 531 and a thread winding wheel 533. The one-way rotation wheel 531 has one-way rotation limit teeth 531a protruding from the outer circumferential surface in the circumferential direction to be lopsided.

As shown in FIGS. 14(b) and 14(c), the one-way rotation limit teeth 531a come into contact with the one-way rotation limit bar 540, and the winder gear 530 is rotated just in the direction that the free end 237 is wound but is not rotated in the direction that the free end 237 is unwound.

The one-way rotation limit bar 540 is accommodated in the limit bar receiving groove 113b and comes into contact with the one-way rotation wheel 531 to limit the rotational direction of the one-way rotation wheel 531. A rotation allowable incline 541, which has the same inclination angle as the one-way rotation limit teeth 531a, is formed at the top of a side of the one-way rotation limit bar 540, and a rotation-prevention horizontal plane 543 is formed at the top.

As shown in FIG. 14(b), when the winder gear 530 is rotated in the direction that the free end 237 is wound, namely, in the counterclockwise direction in the drawing, the one-way rotation limit teeth 531a move along the rotation allowable incline 541, and the rotation is allowed.

On the other hand, as shown in FIG. 14(c), when the winder gear 530 is rotated in the direction that the free end 237 is unwound, namely, in the clockwise direction in the drawing, the rotation-prevention horizontal plane 543 is fit inside a groove between the one-way rotation limit teeth 531a to block the rotation.

Therefore, the winder gear 530 is always rotated just in the direction that the length-adjustable loop 233 of the ligature 230 gets shorter.

The thread winding wheel 533 is disposed at an upper portion of the one-way rotation wheel 531, and the free end 237 of the ligature 230 is joined to the thread winding wheel 533 to be wound on the thread winding wheel 533. A pair of thread insertion holes 533a to which the free end 237 of the ligature 230 is joined are formed in the outer circumferential surface of the thread winding wheel 533. The free end 237 is inserted into one of the thread insertion holes 533a, is passed through the other thread insertion hole 533a, and then, is knotted and is fixed at the thread winding wheel 533.

In the above state, when the thread winding wheel 533 is rotated, the free end 237 is wound on the outer circumferential surface of the thread winding wheel 533 so that the length-adjustable loop 233 gets shorter.

The thread guide cap 537 covers the upper portion of the thread winding wheel 533 and helps prevent the free end 237 wound on the thread winding wheel 533 from being unwound. The position fixing protrusion 537a protrudes from one end of the thread guide cap 537 and is inserted into the winder fixing groove 113a so that the thread guide cap 537 is fixed in its position.

A thread movement tube 537b is formed to be separated from the position fixing protrusion 537a. As shown in FIG. 14(b), the free end 237 exiting the rear end of the needle insertion tube 310 is wound on the thread winding wheel 533 through the thread movement tube 537b.

Therefore, the winder gear 530 and the thread winding wheel 533 formed integrally with the winder gear 530 are rotated in the rotational direction of the winder handle 520, but the thread guide cap 537 is fixed in its position to guide the free end 237 to the thread winding wheel 533.

Now, referring to FIGS. 2 to 19, a process for surgical operation of benign prostatic hyperplasia using the benign prostatic hyperplasia treatment device 1 according to the present invention will be described.

As shown in FIG. 2, the benign prostatic hyperplasia treatment device 1 is sterilized and packaged in the state where it has been assembled completely, and a pair of the benign prostatic hyperplasia treatment device 1 are prepared for the surgical operation.

That is, the needle guide member 340 is prepared in the state where it is combined with the front end of the sheath body 300a. The needle 350 is packaged in the state where it is accommodated in the sheath body 300a. The pusher shaft 361 is packaged in the state where it is accommodated in the needle 350.

The anchor assembly 200 is loaded at the needle slot 351 of the needle 350, and the fixed end 231 and the length-adjustable loop 233 is exposed out of the needle slot 351 as shown in FIG. 6. Moreover, the free end 237 of the ligature 230 is guided to the back along the needle insertion tube 310 of the needle 350 and is extended from the rear of the needle insertion tube 310 to a predetermined length.

In this instance, the free end 237 of the ligature 230 extended to the rear end of the needle insertion tube 310 is connected to the thread winding wheel 533 of the winder gear 530 as shown in FIG. 14(a).

In the preparation state before the surgical operation, as shown in FIG. 10(a), the trigger locking member 440 is located at the back of the locking member movement grooves 115 and 125, and the pusher button 366 is located at the back of the pusher movement slits 112 and 121.

Therefore, as shown in FIG. 12(a), the needle holder 410 is pulled back and the holder position fixing teeth 421a of the holder removable bar 421 of the needle trigger 420 engage with the front of the holder position adjusting teeth 411a so that the needle holder 410 is fixed in its position.

The elastic member 433 is compressed and the trigger locking member 440 is accommodated in the locking shaft receiving ring 429 so that the needle trigger 420 is fixed in its position.

The operator carries out local anesthesia to the urethra using anesthetic gel, spinal anesthesia or general anesthesia. As shown in FIG. 18(a), the urethra (C) is blocked by the enlarged left prostate lobe A and the enlarged right prostate lobe B.

The operator inserts the outer sheath S through a urethral meatus, and the outer sheath S is left inserted till the surgical operation is finished.

As shown in FIG. 18(b), the operator inserts the sheath 300 into the urethra (C) through the outer sheath 300a inserted previously. In this instance, the needle 350 is in the state where it is accommodated in the needle insertion tube 310.

As shown in FIG. 10(a), the operator moves the trigger locking member 440, which is extended out of the handle frame part 100, forwards. Therefore, the trigger locking member 440 gets out of the locking shaft receiving ring 429 of the needle trigger 420 as shown in FIG. 15(a).

In the above state, the operator inspects the inside using the transurethral endoscope 600 inserted into the sheath 300, and checks the positions where the anchors 210 and 220 will be placed. The positions for placing the anchors 210 and 220 may be determined based on anatomical points, such as the bladder neck or verumontanum.

The sheath 300 is tilted at an angle of 20 degrees or more toward the left prostate lobe. This is just an example, and the operator can select whether he or she wants to treat the left or the right side first according to his or her independent judgment.

Furthermore, as shown in FIG. 12(b), the operator rotates the trigger manipulation button 427 of the needle trigger 420 upwards so that the holder position fixing teeth 421a of the holder removable bar 421 are free from the holder position adjusting teeth 411a of the needle holder 410.

Therefore, the needle holder 410 is deployed forwards by elastic force of the elastic member 433, and as shown in FIG. 18(c), the needle 350 is deployed outwards from the needle guide member 340 and comes out of the prostate gland after penetrating through the prostate gland.

In this instance, as shown in FIG. 16(a), the first anchor 210 and the second anchor 220 are accommodated in the needle slot 351 in consecutive order, and the pusher shaft 361 is inserted at the rear end of the second anchor 220. The first anchor 210 and the second anchor 220 inside the needle 350 are fixed in their positions unless the operator forcibly applies force since the bent plate 217 exerts force to be bent.

The operator pushes the pusher button 366, which is extended out of the handle frame part 100, forwards. Therefore, as shown in FIG. 15(c), the pusher button 366 moves forwards along the pusher button movement rail 411b.

In this instance, the pusher tail 367 is caught at the second groove 416b, and the operator stops applying force to the pusher button 366.

When the pusher tail 367 is caught at the second groove 416b, the pusher shaft 361 pushes the second anchor 220 forwards, and as shown in FIG. 16(b), the first anchor 210 is released from the needle 350. As shown in FIG. 18(d), the first anchor 210 released from the needle 350 is deployed on the outer surface of the upper portion of the left prostate lobe A.

When the deployment of the first anchor 210 is completed, the operator pulls back the pulling lever 413 so that the holder position fixing teeth 421a of the needle trigger 420 engage with the front of the holder position adjusting teeth 411a. Therefore, the needle 350 is returned to the inside of the needle guide member 340.

The operator moves the sheath 300 downwards, and moves the needle guide member 340 to the position where the second anchor 220 will be placed. Then, the operator rotates the trigger manipulation button 427 of the needle trigger 420 upwards to deploy the needle holder 410 forwards, and makes the needle 350 penetrate through the lower portion of the left prostate lobe A.

In addition, as shown in FIG. 17(a), the operator manipulates the pusher button 366 forwards, and the pusher tail 367 fits inside the third groove 416c. As shown in FIG. 17(b), due to the forward movement of the pusher button 366 the pusher shaft 361 pushes the rear end of the second anchor 220 so that the second anchor 220 is released from the needle 350.

As shown in FIG. 19(a), the second anchor 220 released from the needle 350 is placed on the outer surface of the lower portion of the left prostate lobe A. In this instance, the first anchor 210 and the second anchor 220 are connected with each other by the ligature 230, and the free end 237 is wound on the thread winder 500 through the needle insertion tube 310.

As shown in FIG. 19(a), because the length of the length-adjustable loop 233 is not adjusted in the state where the first anchor 210 and the second anchor 220 are placed on the outer surface of the prostate gland, the ligature 230 is positioned loosely so that the prostate tissue is not compressed.

As shown in FIG. 19(b), the operator inspects the inside with the endoscope and rotates the winder handle 520 so that the free end 237 is wound on the thread winding wheel 533. The free end 237 is wound on the thread winding wheel 533, the length-adjustable loop 233 gets shorter, and the anchor assembly 200 compresses the left prostate lobe A.

The operator checks how the anchor assembly 200 opens the urethra (C) by compressing the left prostate lobe A, and then, as shown in FIG. 10(b), pushes the blade pressing button 375 backwards.

As shown in FIG. 9(b), the blade plate 371 slides toward the back of the needle outlet 346, and the free end 237 of the ligature 230 is inserted into the blade slit 371b of the blade plate 371 and is cut. The free end 237 of the cut ligature 230 is 1 mm or less in length, and can be embedded in the prostate tissue. Therefore, as shown in FIG. 19(c), the anchor assembly 200 compresses the left prostate lobe A to open the prostatic urethra. Then, the surgical operation is finished.

The operator removes the sheath 300 out of the urethra, and then deploys the anchor assembly 200 to the right prostate lobe B in the same way as the left prostate lobe A using a new benign prostatic hyperplasia treatment device 1.

As shown in FIG. 19(d), a pair of the anchor assemblies 200 is deployed at the left prostate lobe A and the right prostate lobe B to open the urethra C. In this instance, the anchor assemblies 200 continuously compress the prostate tissues in the form of a "U" character or an oval shape connecting the first anchor 210, the second anchor 220 and the ligature 230 with one another. Therefore, the length of the urethra C opened by being pressed by the ligature 230 can be adjusted and the width d of the urethra pressed can be also adjusted.

Meanwhile, the benign prostatic hyperplasia treatment device 1 according to the present invention has been described in such a way that the first anchor 210 is deployed first and the second anchor 220 is deployed later, but this is just an example, and as occasion demands, the second anchor 220 may be deployed first, and then, the first anchor 210 may be deployed later.

In the meantime, the benign prostatic hyperplasia treatment device 1 according to the present invention has been described in such a way that the first anchor 210 is deployed at the upper portion of the prostate gland and the second anchor 220 is deployed at the lower portion of the prostate gland, but this is just an example, and the second anchor 220 may be deployed at the upper portion of the prostate gland and the first anchor 210 may be deployed at the lower portion.

Meanwhile, in the benign prostatic hyperplasia treatment device 1 according to the present invention, the needle holder 410 is deployed by elastic force of the elastic member 433, and the needle 350 is inserted into the prostate gland. However, as occasion demands, the operator may push the needle holder 410 by hand to adjust the position of the needle 350.

Figure 20:
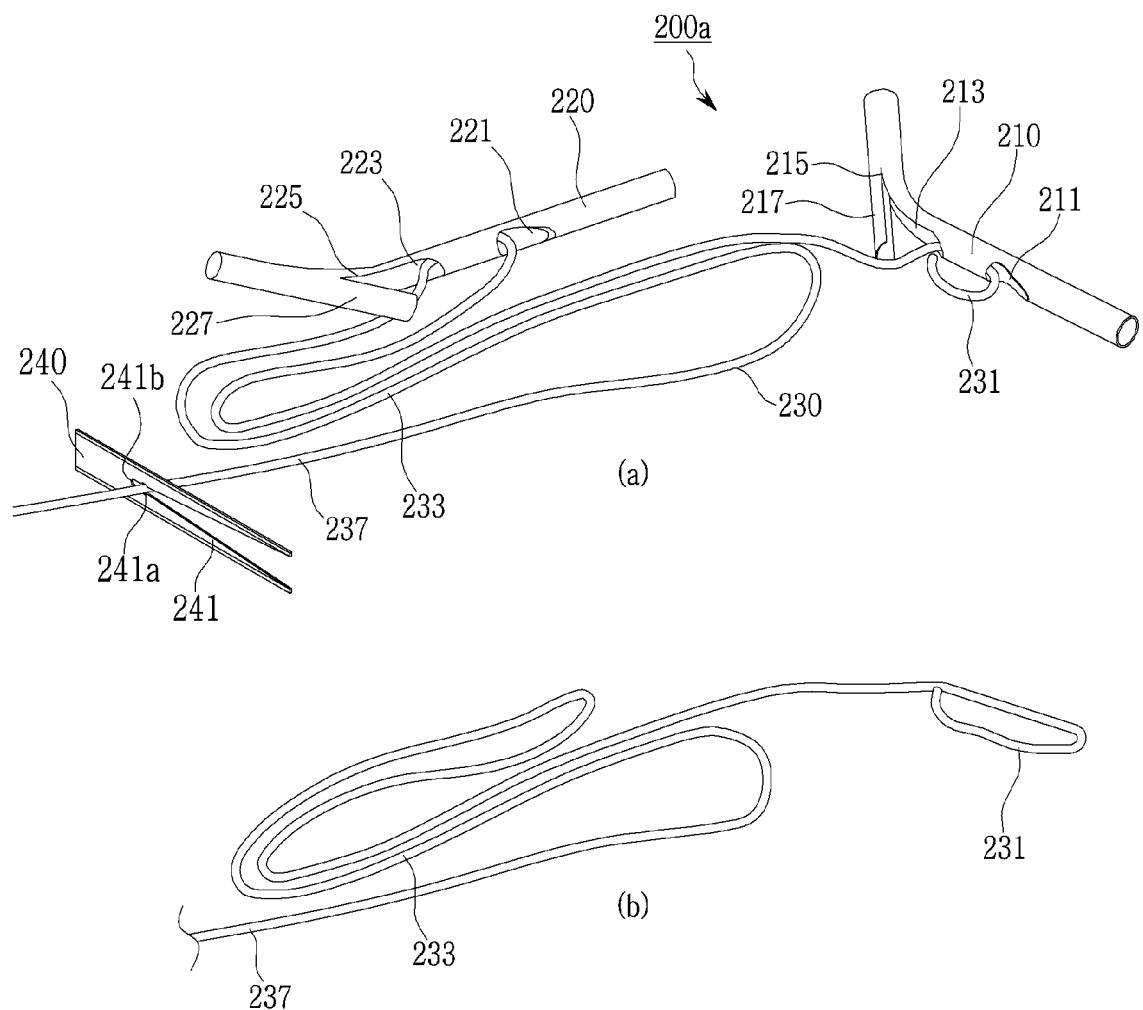
FIG. 20 is a view showing an anchor assembly of a benign prostatic hyperplasia treatment device according to a first modification of the present invention.
Figure 21:
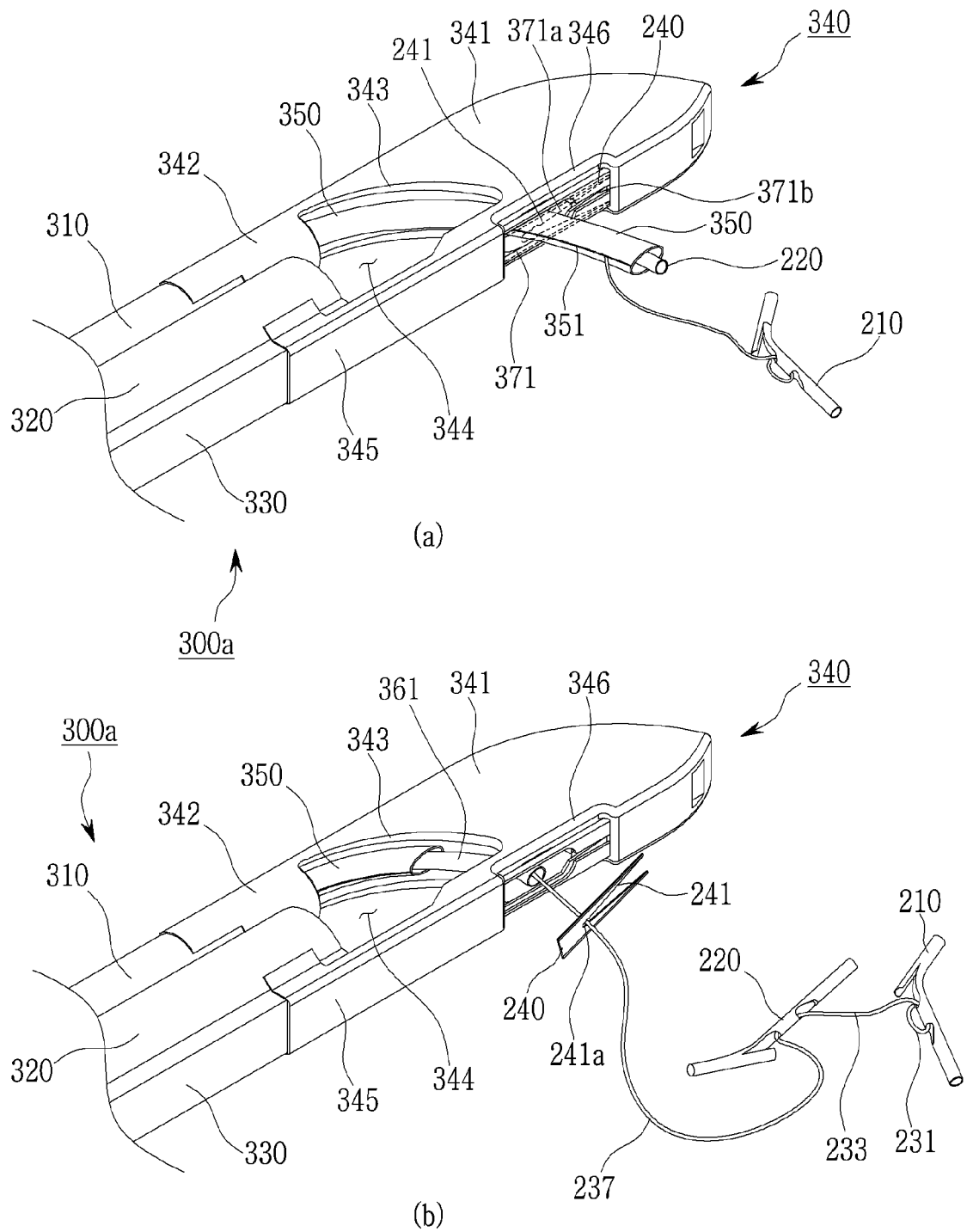
FIG. 21 is an exemplary view showing a treatment process of the anchor assembly according to the first modification of the present invention.
Figure 22:
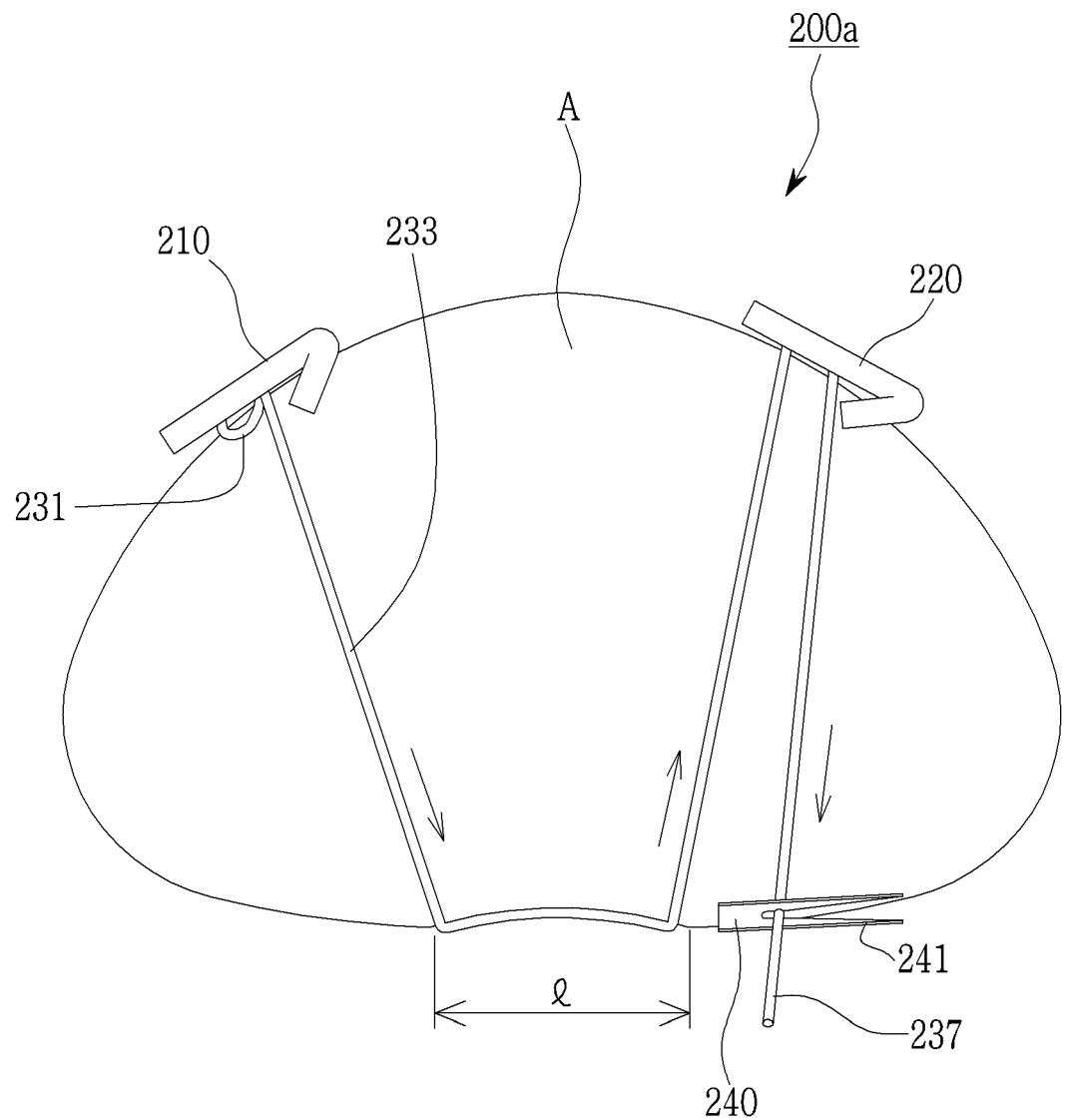
FIG. 22 is an exemplary view showing a state where the anchor assembly of the benign prostatic hyperplasia treatment device according to the first modification of the present invention is deployed at the left prostate lobe.

In the meantime, FIG. 20 is a view showing an anchor assembly 200a of a benign prostatic hyperplasia treatment device according to a first modification of the present invention, FIG. 21 is an exemplary view showing a treatment process of the anchor assembly 200a according to the first modification of the present invention, and FIG. 22 is an exemplary view showing a state where the anchor assembly 200a of the benign prostatic hyperplasia treatment device according to the first modification of the present invention is deployed at the left prostate lobe A.

In the case of the anchor assembly 200 according to the embodiment of the present invention, the first anchor 210 and the second anchor 220 are respectively arranged on the outer surfaces of the prostate lobes to be spaced apart from each other, and the length-adjustable loop 233 connecting the first anchor 210 and the second anchor 220 is adjusted in length by the slip knot 235 and continuously compresses the prostate tissue.

On the other hand, the anchor assembly 200a according to the first modification of the present invention continuously compresses the prostate tissue while adjusting the length of the length-adjustable loop 233 without the slip knot 235. In order to achieve the above, the anchor assembly 200a according to the first modification of the present invention includes a lock anchor 240 besides the first anchor 210 and the second anchor 220.

As shown in FIGS. 20(a) and 20(b), the anchor assembly 200a has the first anchor 210 and the second anchor 220, wherein the first anchor 210 is fixed at the fixed end 231, and the second anchor 220 is connected to the fixed end 231 through the length-adjustable loop 233. Additionally, the length-adjustable loop 233 is connected to the free end 237.

The lock anchor 240 combined with the free end 237, and as shown in FIG. 22, is located in the inner urethral region of the prostate lobe A in a direction opposed to the second anchor 220 to fix the position of the free end 237.

The lock anchor 240 is made with a plate-shaped material, and has a thread guide groove 241 cut inwards from an end portion. The thread guide groove 241 is formed in a "V" character so as to be gradually wider from the inside to the outside. The thread guide groove 241 has a thread fixing groove 241a formed on an inner face 241b so that the ligature 230 is fit and fixed therein.

As shown in FIG. 21(a), the lock anchor 240 is arranged inside the blade plate 371 in parallel with the blade plate 371. The thread guide groove 241 is arranged in such a way that the needle 350 is not interfered when the needle 250 enters the needle discharge hole 371a and is discharged from the needle discharge hole 371a.

The lock anchor 240 maintains a state where the lock anchor 240 is joined to the inner wall surface of the blade plate 371 till the first anchor 210 and the second anchor 220 are located outside the prostate gland. The sheath 300 is moved toward the inside of the prostate gland, namely, the urethra (C), and then, is moved to face the second anchor 220. After that, as shown in FIG. 21(b), when the operator compresses the pusher shaft 361 out of the needle 350, the lock anchor 240 on the rear surface of the blade plate 371 is discharged to the urethra (C) through the needle discharge hole 371a. In this instance, the free end 237 connected with the second anchor 220 is guided to the thread guide groove 241 of the lock anchor 240 to be inserted into the thread fixing groove 241a.

After checking that the lock anchor 240 is located inside the urethra (C) with the endoscope, the operator rotates the winder handle 520 so that the free end 237 is wound on the thread winding wheel 533. Accordingly, the length-adjustable loop 233 gets shorter and compresses the prostate gland to open the urethra (C). After that, the blade plate 371 is moved backwards so that the free end 237 is cut.

The anchor assembly 200a according to the first modification has the length-adjustable loop 233 which connects the first anchor 210, the second anchor 220 and the lock anchor 240 with one another without using the slip knot 235, thereby continuously compressing a predetermined portion of the prostate gland by adjusting the length of the length-adjustable loop.

Figure 23:
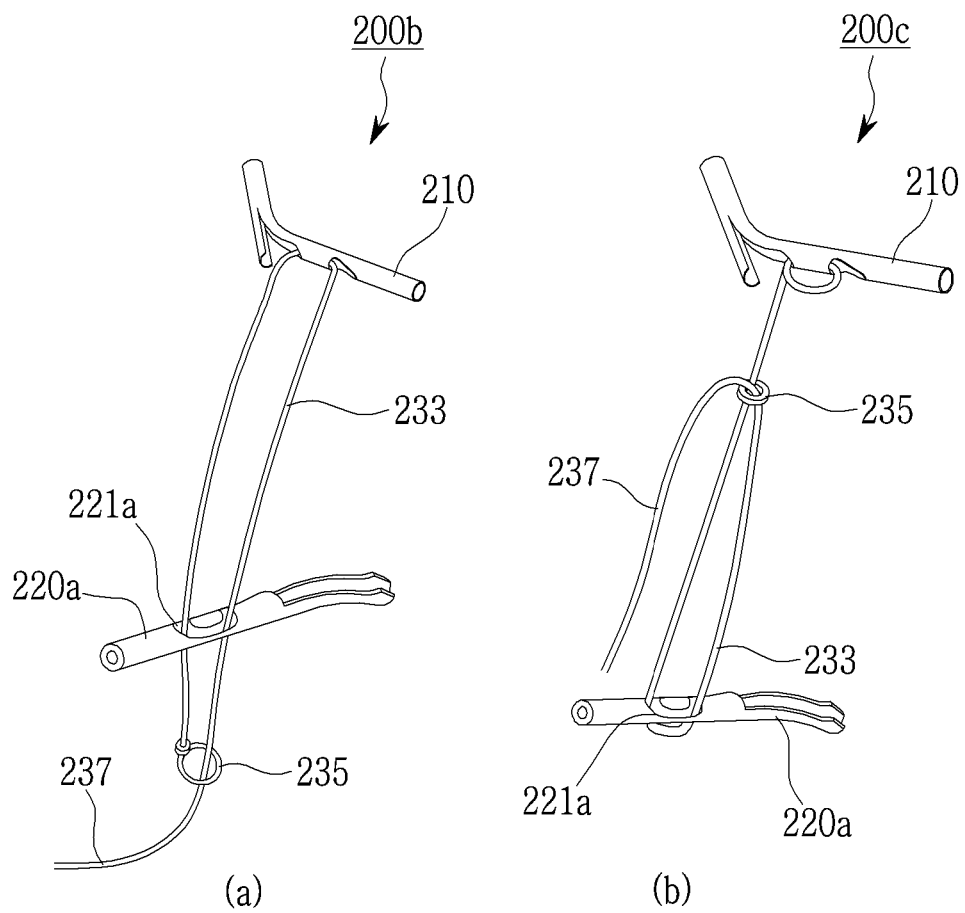
FIG. 23 is a view showing anchor assemblies of according to a second modification and a third modification of the present invention.
Figure 24:
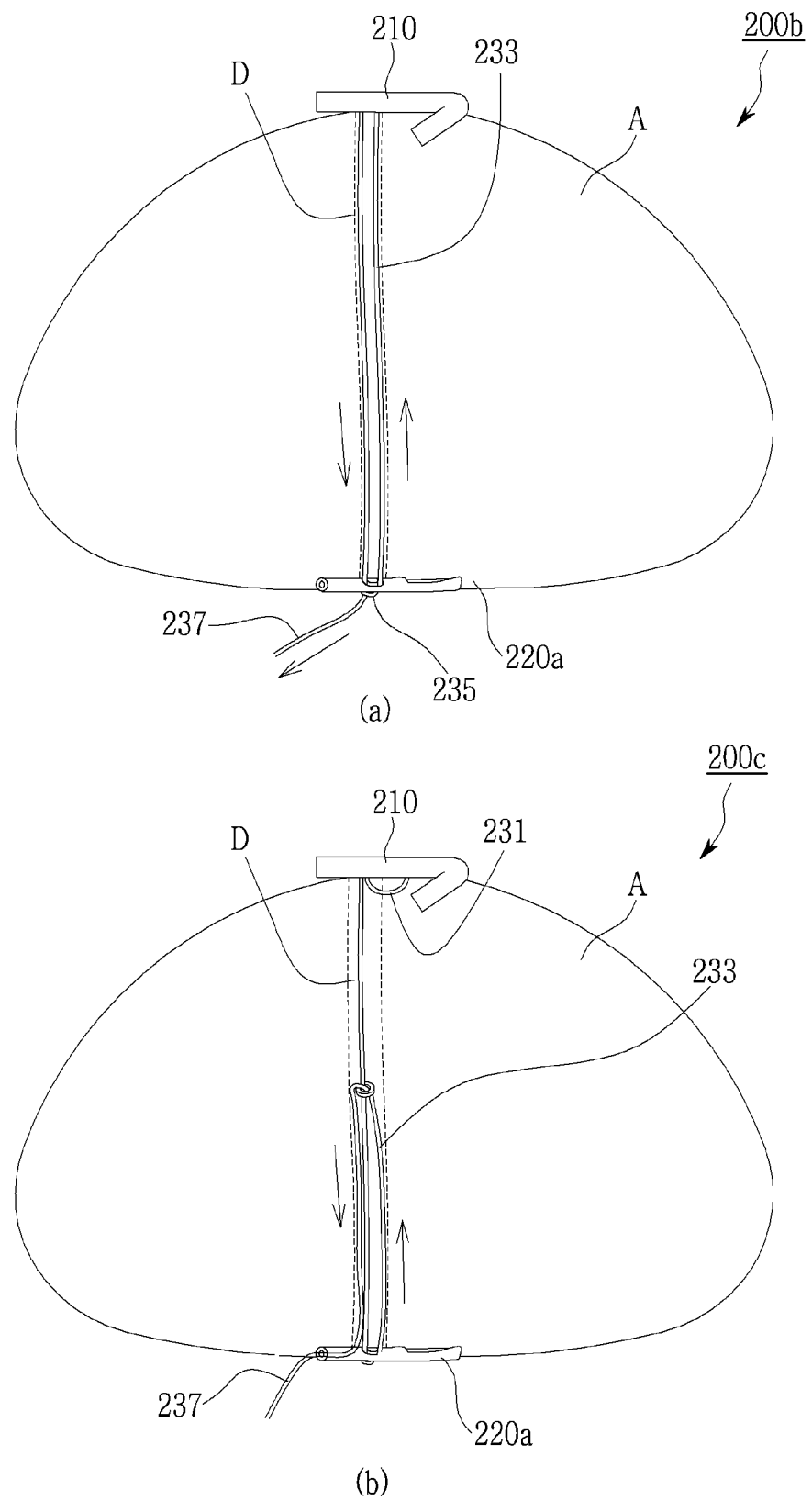
FIG. 24 is an exemplary view showing a state where the anchor assembly according to the second modification of the present invention is deployed at the left prostate lobe and a state where the anchor assembly according to the third modification of the present invention is deployed at the left prostate lobe.

Meanwhile, FIG. 23 is a view showing anchor assemblies 200b of according to a second modification and a third modification of the present invention, and FIG. 24 is an exemplary view showing a state where the anchor assembly 200b according to the second modification of the present invention is deployed at the left prostate lobe A and a state where the anchor assembly according to the third modification of the present invention is deployed at the left prostate lobe A.

In the case of the anchor assembly 200b according to the second modification of the present invention, a first anchor 210 is arranged outside the prostate lobe A, and a second anchor 220a is arranged to face the inside of the prostate lobe A, namely, the urethra (C). An end of the length-adjustable loop 233 is combined to surround the inside of the first thread coupling hole 211 and a second thread coupling hole 213 of the first anchor 210, and the other end extends to the second anchor 220a. The other end of the length-adjustable loop 233 is connected with the free end 237 below the second anchor 220a by the slip knot 235.

The second anchor 220a as a thread coupling groove 221a formed in a round ring shape on the plate surface thereof so that the length-adjustable loop 233 penetrates downwards to be connected with the free end 237.

As shown in FIG. 24(a), the first anchor 210 is arranged outside the prostate lobe A, and the second anchor 220a is arranged inside the prostate lobe A. when the free end 237 is wound, the length-adjustable loop 233 connected with the slip knot 235 gets shorter, and the second anchor 220a compresses the prostate tissue to open the urethra. In this instance, the length-adjustable loop 233 is located inside a penetration path D through which the needle 350 passes.

Meanwhile, compared with the anchor assembly 200b according to the second modification of the present invention, the anchor assembly 200c according to the third modification of the present invention has the slip knot 235 located between the first anchor 210 and the second anchor 220a.

The first anchor 210 is fixed by the fixed end 231, and the length-adjustable loop 233 extends to be wound on the thread coupling groove 221a of the second anchor 220a is connected with the free end 237 through the slip knot 235.

As shown in FIG. 24(b), when the operator pulls the free end 237, the length-adjustable loop 233 gets shorter, and the second anchor 220a compresses the prostate tissue to open the urethra.

Figure 25:
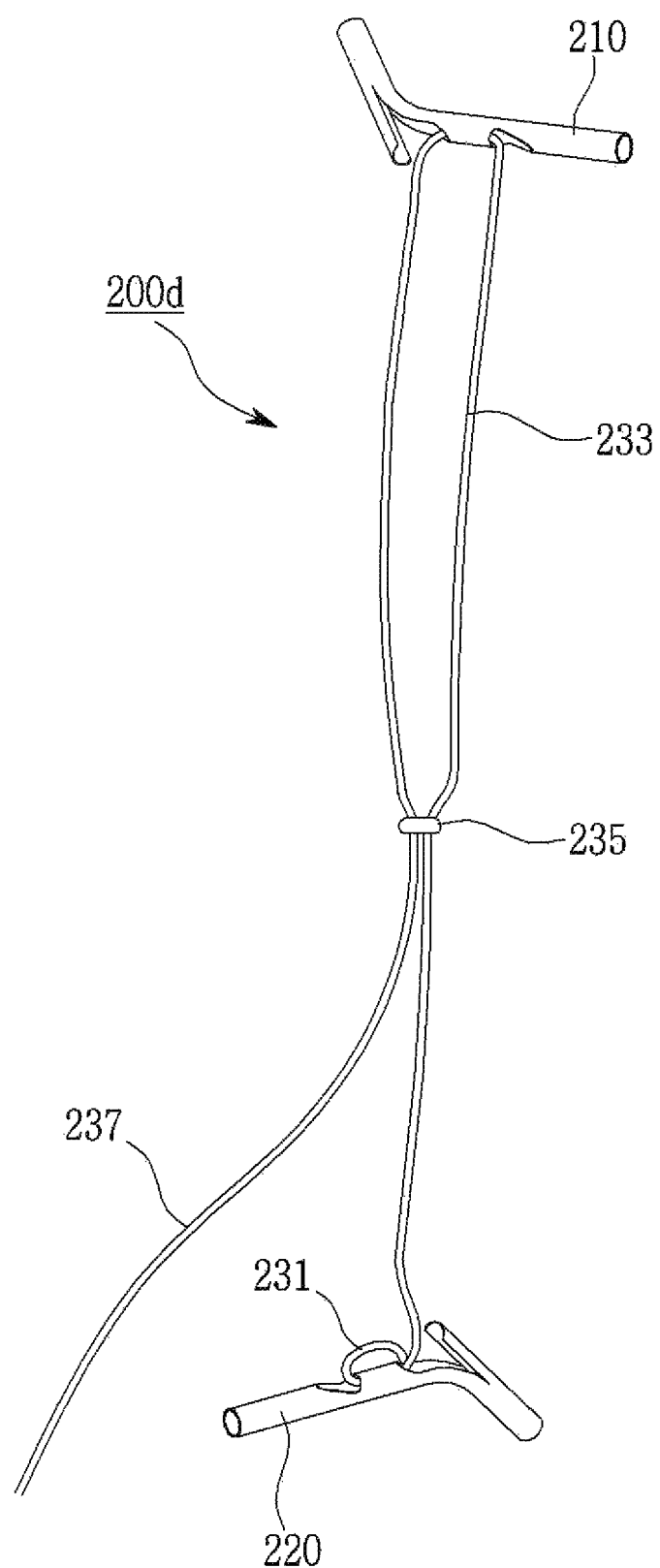
FIG. 25 is a view showing an anchor assembly of according to a fourth modification of the present invention.
Figure 26:
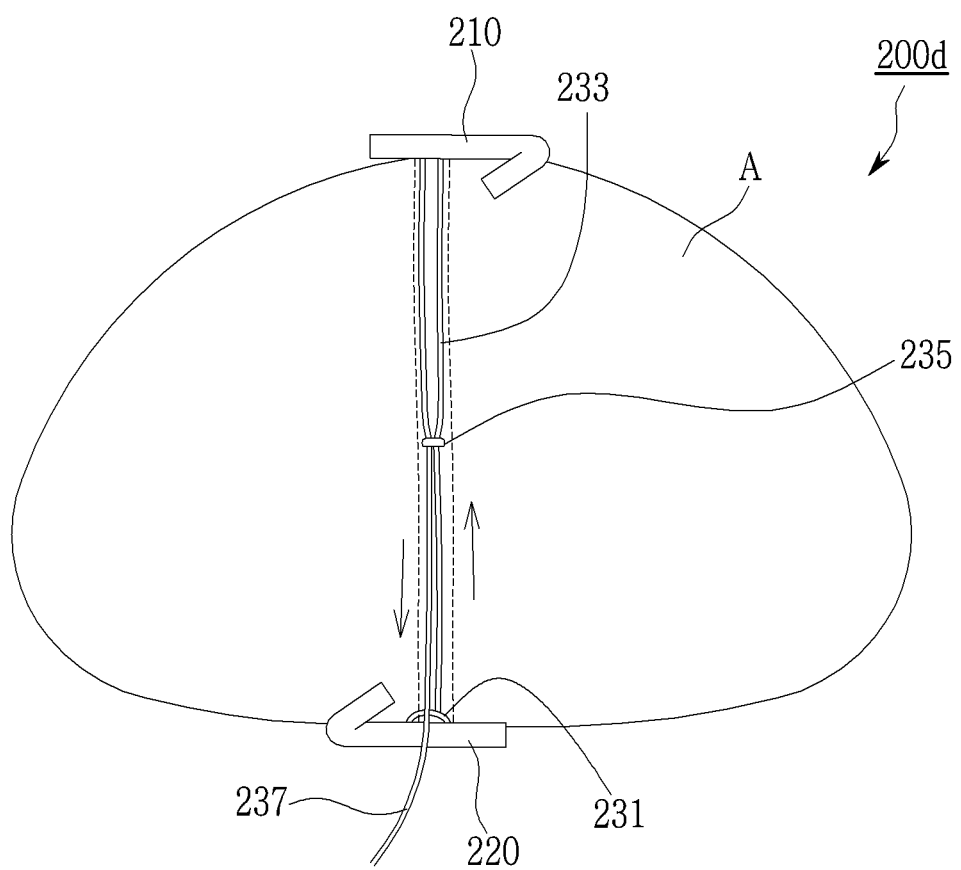
FIG. 26 is an exemplary view showing a state where the anchor assembly according to the fourth modification of the present invention is deployed at the left prostate lobe.

In the meantime, FIG. 25 is a view showing an anchor assembly 200d of according to a fourth modification of the present invention, and FIG. 24 is an exemplary view showing a state where the anchor assembly 200d according to the fourth modification of the present invention is deployed at the left prostate lobe A.

In the case of the anchor assembly 200d according to the fourth modification of the present invention, the fixed end 231 of the ligature 230 is fixed to the second anchor 220, and the length-adjustable loop 233 is joined to the first anchor 210. The length-adjustable loop 233 is connected with the free end 237 by the slip knot 235 between the first anchor 210 and the second anchor 220.

In the case of the anchor assembly 200d according to the fourth modification of the present invention, only the first anchor 210 is accommodated in the needle 350, and the second anchor 220 is located inside the blade plate 371 or at an entrance of the sheath 300 in a semifixed state.

When the operator deploys the first anchor 210 outside the prostate lobe A and rotates the winder handle 520 to wind the free end 237 on the thread winding wheel 533, the free end 237 gets shorter and the length-adjustable loop 233 is pulled. So, the second anchor 220 is discharged out of the sheath 300 and is located inside the prostate lobe A by power pulling the length-adjustable loop 233.

In the above state, when the operator pulls the free end 237 to make the length-adjustable loop 233 shorter, the second anchor 220 is pressed to compress the prostate lobe A, thereby opening the urethra (C).

As described above, compared with the conventional treatment method of partially compressing the prostate tissue, the benign prostatic hyperplasia treatment device according to the present invention increases urine flow rate since the prostate tissues compressed by the ligature and a pair of the anchors are continuous, and it is more effective for patients who have a large prostate gland.

Moreover, the benign prostatic hyperplasia treatment device according to the present invention can adjust the intensity with which to compress the prostate gland as much as the operator wants since the operator can adjust the length of the ligature by winding the free end of the ligature.

Therefore, the benign prostatic hyperplasia treatment device according to the present invention can adjust how to compress the prostate gland according to various symptoms of the benign prostatic hyperplasia presented by patients.

A treatment method using the benign prostatic hyperplasia treatment device according to the present invention does not need general anesthesia or long operation time like laser surgery or electrical surgery using thermal energy.

Additionally, the benign prostatic hyperplasia treatment device according to the present invention makes quick operation time and local anesthesia possible through the simple anchor installation method, and is not accompanied by side effects, such as retrograde ejaculation, impotence or hematuria, since the prostate tissues are not cut. In addition, because the benign prostatic hyperplasia treatment device according to the present invention is minimally invasive, if it is ineffective, a patient can have another operation any time.

The technical thoughts of the present invention have been described hereinafter.

It is to be appreciated that those skilled in the art can change or modify the embodiments from the above description in various ways. Even if it is not clearly illustrated or described herein, it is to be appreciated that those skilled in the art can change or modify the embodiments from the above description in various ways without departing from the scope and spirit of the present invention, and such changes and modifications belong to the scope of the present invention. While the present invention has been described with reference to the particular illustrative embodiments, it is not to be restricted by the embodiments but only by the appended claims.

[Explanation of essential reference numerals in drawings]

1: benign prostatic hyperplasia treatment device
100: handle frame part
110: left frame
111: needle manipulating part receiving groove
112: left pusher movement slit

[Explanation of essential reference numerals in drawings]

113: thread winder receiving recess
113a: winder fixing groove
113b: limit bar receiving groove
113c: shaft combining hole
114: left blade button movement slit
115: left locking member movement groove
116: left lever movement path
117: left endoscope insertion hole
118: trigger rotating shaft combining hole
119: sheath combining plate insertion groove
120: right frame
121: right pusher movement slit
123: right blade button movement slit
125: right locking member movement groove
126: right lever movement path
127: right endoscope insertion hole
200: anchor assembly
210: first anchor
211: first thread hole
213: second thread hole
215: bent slit
220, 220a: second anchor
221a: thread coupling groove
230: ligature
231: fixed end
233: length-adjustable loop
235: slip knot
237: free end
240: lock anchor
241: thread guide groove
241a: thread fixing groove
241b: inner face
300: sheath
310: needle insertion tube
320: endoscope insertion tube
330: blade shaft movement tube
340: needle guide member
341: guide body
342: needle insertion tube connecting tube
343: needle guide curved surface
344: needle exposure hole
345: blade shaft connecting tube
346: needle outlet
350: needle
351: needle slot
360: pusher
361: pusher shaft
363: pusher holder
365: pusher button shaft
366: pusher button
367: pusher tail
370: needle blade part
371: blade plate
371a: needle discharge hole
371b: blade slit
373: blade plate connecting shaft
375: blade pressing button
380: sheath fixing member
381: sheath combining plate
381a: combining protrusion
383: sheath combining plate
383a: hook locking ring
385: fixing ring
385a: locking hook
400: needle manipulation part
410: needle holder
411: horizontal bar
411a: holder position adjusting teeth
411b: pusher button movement rail
411c: sheath insertion hole
413: pulling lever
413a: support shaft insertion hole
415: upper combining bar
416: tail position fixing rail
416a: first groove
416b: second groove
416c: third groove
420: needle trigger
421: holder removable bar
421a: holder position fixing teeth
423: trigger rotating shaft
425: frame support bar
425a: elastic member combining rib
426: trigger return spring
426a: frame fixing member
427: trigger manipulation button
429: locking shaft receiving ring
430: elastic holder support part
431: elastic member support shaft
431a: shaft position fixing plate
433: elastic member
440: trigger locking member
500: thread winder
510: winder shaft
511: first holder bar
513: second holder bar
515: key
520: winder handle
521: holder combining wheel
521a: internal combining member insertion hole
523: holder combining groove
530: winder gear
531: one-way rotation wheel
531a: one-way rotation limit teeth
533: thread winding wheel
533a: thread insertion hole
535: shaft insertion hole
535a: key hole
537: thread guide cap
537a: position fixing protrusion
537b: thread movement tube
540: one-way rotation limit bar
541: rotation allowable incline
543: rotation-prevention horizontal plane
550: winder handle cover
551: external combining member insertion hole
600: transurethral endoscope
610: transurethral endoscope inlet
A, B: prostate lobe
C: urethra
S: outer sheath

What is claimed is:

1. A benign prostatic hyperplasia treatment device comprising:
   anchor assemblies including a first anchor configured to be arranged at the outer surface of the prostate gland, which is configured to obstruct the prostatic urethra, a second anchor configured to be arranged inside the prostate gland to be opposed to the first anchor, and a ligature connecting the first anchor and the second anchor with each other so that the second anchor configured to compress the prostate tissue to secure the opening of the prostatic urethra;
   a sheath configured to be inserted into the urethra and having a needle, which guides the anchor assembly to be deployed at the prostate gland;
   a needle manipulation part for manipulating movement of the needle so that the needle is deployed through an end portion of the sheath;
   a thread winder disposed at one side of the needle manipulation part and winding the ligature thereon to adjust intensity with which the anchor assemblies is configured to compress the prostate gland; and
   a handle frame part which supports the end portion of the sheath, the needle manipulation part and the thread winder and is configured to be grasped by an operator,
   wherein the ligature includes: a length-adjustable loop joined to the first anchor and the second anchor to be adjustable in length; a free end extending from the length-adjustable loop; and a slip knot for connecting the length-adjustable loop to the free end so as to adjust the length of the length-adjustable loop, and
   wherein the thread winder winds the free end to adjust the length of the length-adjustable loop so that the second anchor is configured to compress the prostate tissue.

2. The benign prostatic hyperplasia treatment device according to claim 1, wherein the slip knot is formed below the second anchor or is formed between the first anchor and the second anchor.

3. The benign prostatic hyperplasia treatment device according to claim 1, wherein the first anchor is accommodated in the needle, and the second anchor is joined to an entrance region of the sheath.

\* \* \* \* \*